(12) United States Patent
Smith et al.

(10) Patent No.: US 6,743,240 B2
(45) Date of Patent: Jun. 1, 2004

(54) FLEXIBLE SURGICAL DEVICE HAVING A ROTATABLE END EFFECTOR ASSEMBLY

(75) Inventors: Kevin W. Smith, Coral Gables, FL (US); Robert Sixto, Jr., Miami, FL (US); Juergen A. Kortenbach, Miami Springs, FL (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 312 days.

(21) Appl. No.: 10/010,904

(22) Filed: Dec. 6, 2001

(65) Prior Publication Data

US 2002/0198540 A1 Dec. 26, 2002

Related U.S. Application Data

(63) Continuation-in-part of application No. 09/891,775, filed on Jun. 25, 2001.

(51) Int. Cl.$^7$ .............................................. A61B 17/10
(52) U.S. Cl. .................... 606/142; 606/157; 600/104
(58) Field of Search ................................. 606/142, 143, 606/139, 205, 206, 104, 157, 158; 227/175.1; 600/106, 137, 104

(56) References Cited

U.S. PATENT DOCUMENTS

| | | | |
|---|---|---|---|
| 4,038,987 A | 8/1977 | Komiya | 128/321 |
| 5,174,276 A | 12/1992 | Crockard | 128/4 |
| 5,222,961 A | 6/1993 | Nakao et al. | 606/143 |
| 5,318,528 A * | 6/1994 | Heaven et al. | 604/95.01 |
| 5,433,721 A | 7/1995 | Hooven et al. | 606/143 |
| 5,482,054 A | 1/1996 | Slater et al. | 128/751 |
| 5,624,379 A * | 4/1997 | Ganz et al. | 600/104 |
| 5,667,517 A | 9/1997 | Hooven | 606/151 |
| 5,673,841 A | 10/1997 | Schulze et al. | 227/175.1 |
| 5,722,421 A | 3/1998 | Francese et al. | 128/751 |
| 5,897,507 A | 4/1999 | Kortenbach et al. | 600/562 |
| 6,149,660 A | 11/2000 | Laufer et al. | 606/143 |

OTHER PUBLICATIONS

"What Endoscopic Accessories Do We Really Need?", C. Paul Swain, Emerging Technologies in Gastrointestinal Encoscopy, Gastrointest. Endosc., vol. 7, No. 2, pp. 313–330 (Apr. 1997).

* cited by examiner

*Primary Examiner*—Julian W. Woo
(74) *Attorney, Agent, or Firm*—Gordon & Jacobson, P.C.

(57) ABSTRACT

A flexible clip applier includes a flat wire wound tubular coil, a pair of jaws at the end of the coil, end effector wires extending through the coil and coupled to the jaws, and a clip-advancing wire extending through the coil. A clip chamber is defined in the distal end of the coil. The clip-advancing wire includes a clip pusher which advances a clip into the jaws when the clip-advancing wire is moved distally. The jaws include channels in which a distalmost clip rides when the jaws are closed and the pusher is advanced, thereby causing the distalmost clip to be pushed over the tissue, and a distal anvil which operate to bend a portion of the clip to facilitate its retention on the clamped tissue. Rotation of the clip-advancing wire effects rotation of the jaws are rotatable about a longitudinal axis of the device.

16 Claims, 21 Drawing Sheets

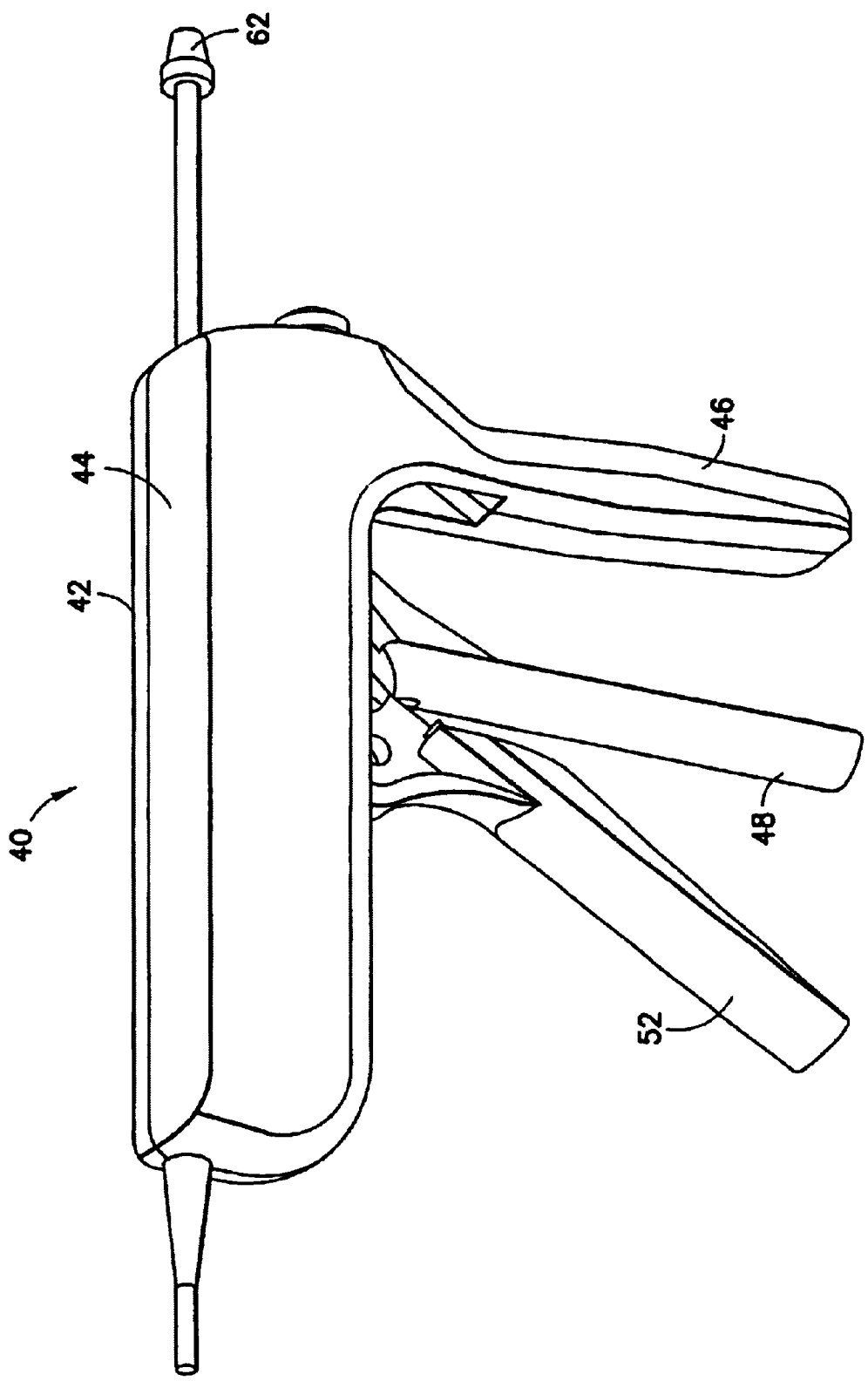

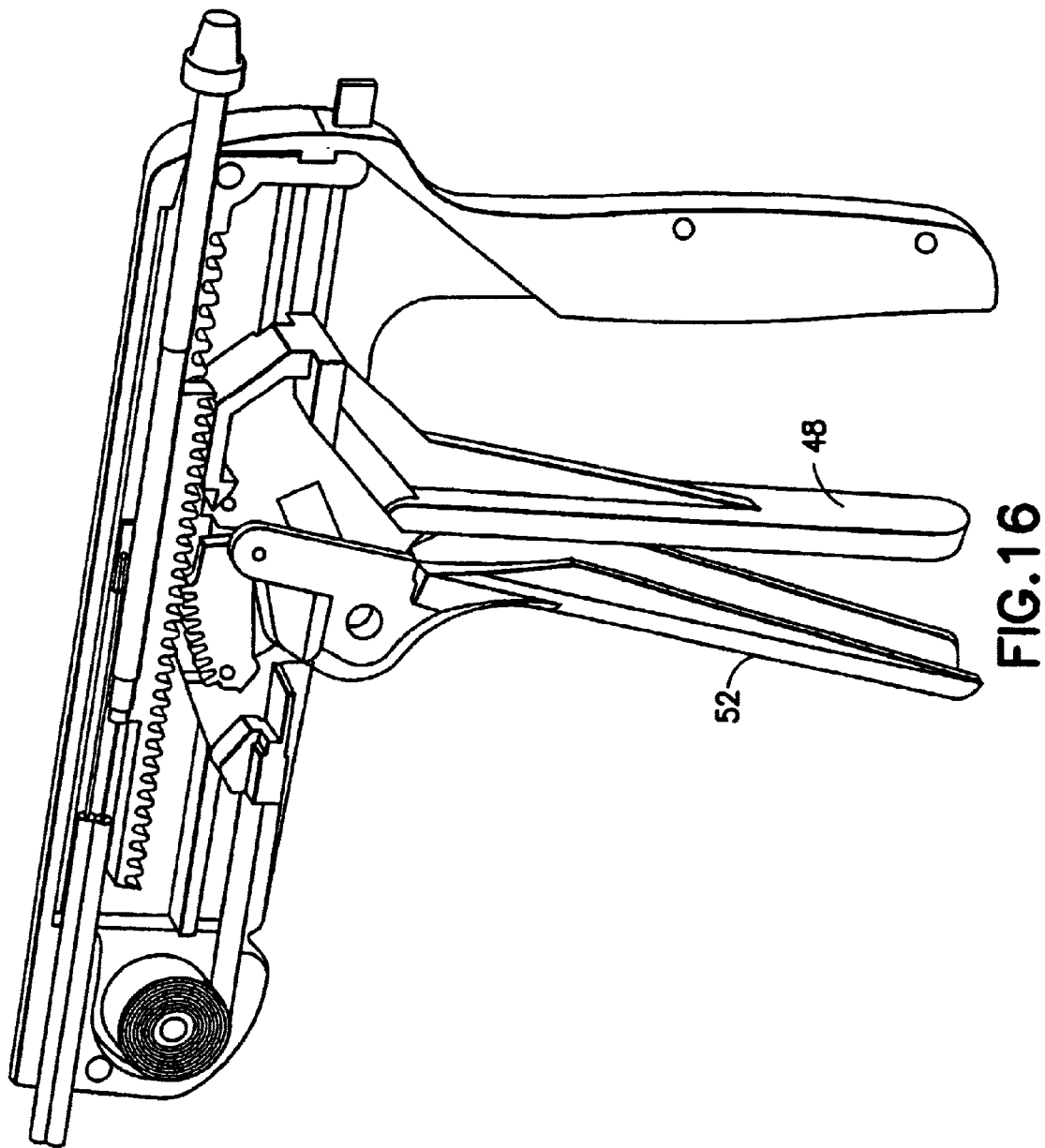

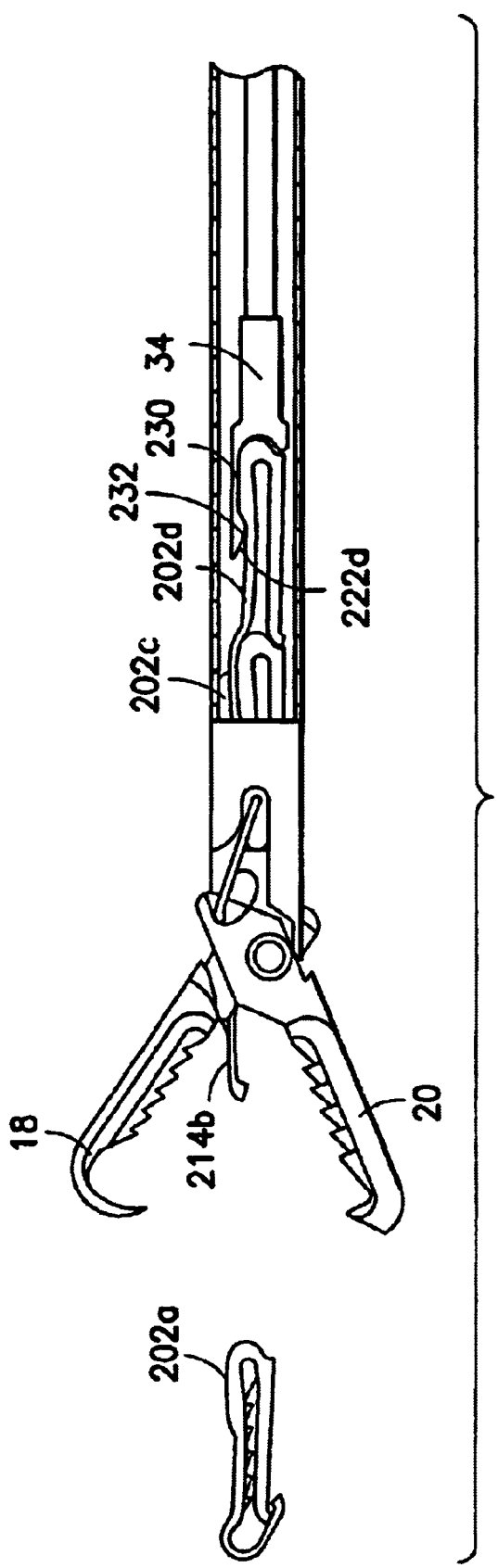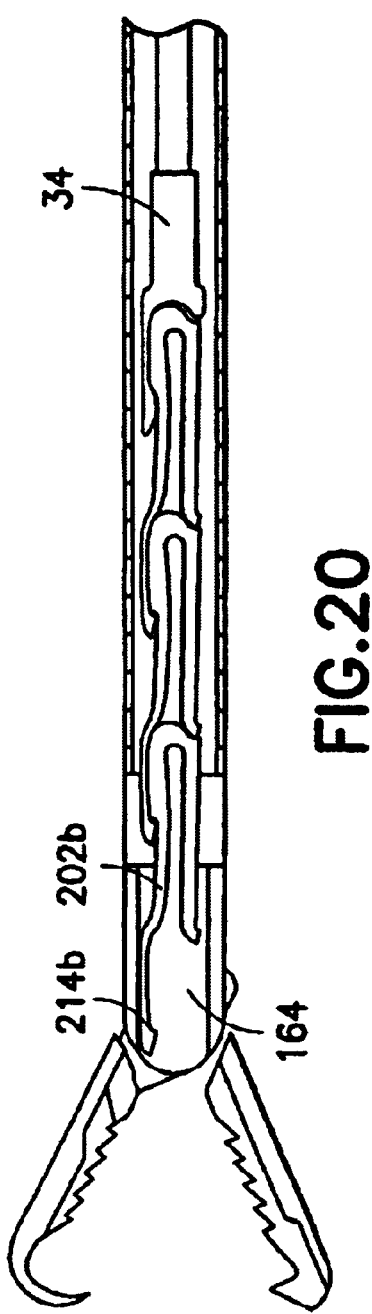
FIG.19
FIG.20

| | RUN #1 | RUN #2 | RUN #3 | RUN #4 | RUN #5 | RUN #6 | RUN #7 | RUN #8 | RUN #9 | RUN #10 | RUN #11 |
|---|---|---|---|---|---|---|---|---|---|---|---|
| COIL O.D. | 0.09 | 0.09 | 0.09 | 0.09 | 0.09 | 0.09 | 0.09 | 0.09 | 0.086 | 0.086 | 0.083 |
| COIL I.D. | 0.06 | 0.06 | 0.06 | 0.06 | 0.06 | 0.06 | 0.06 | 0.053 | 0.053 | 0.054 | 0.054 |
| CLIP ADVANCING WIRE O.D. | 0.017 | 0.017 | 0.017 | 0.015 | 0.02 | 0.02 | 0.02 | 0.017 | 0.017 | 0.017 | 0.017 |
| END EFFECTS WIRE O.D. | 0.011 | 0.011 | 0.011 | 0.011 | 0.011 | 0.011 | 0.011 | 0.009 | 0.009 | 0.009 | 0.009 |
| BARRIER SHEATH | YES | YES | YES | YES | YES | YES | YES | YES | YES | YES | YES |
| | RUN #1 | RUN #2 | RUN #3 | RUN #4 | RUN #5 | RUN #6 | RUN #7 | RUN #8 | RUN #9 | RUN #10 | RUN #11 |
| 1 lb | 0.46 | 0.24 | 0.32 | 0.54 | 0.59 | 0.56 | 0.45 | 0.87 | 0.4 | 0.57 | 0.77 |
| 2 lb | 1.19 | 0.75 | 0.9 | 1.07 | 1.07 | 1.07 | 0.69 | 1.62 | 1.12 | 1.02 | 1 |
| 3 lb | 1.67 | 1.24 | 1.44 | 1.51 | 1.9 | 1.7 | 1.02 | 2.07 | 1.61 | 1.39 | 1.77 |
| 4 lb | 2.19 | 1.81 | 1.98 | 2.62 | 2.3 | 2.6 | 1.51 | 2.61 | 2.01 | 2.09 | 2.76 |
| 5 lb | 2.74 | 2.35 | 2.59 | 2.05 | 3.07 | 2.98 | 2.26 | 3.5 | 2.44 | 3.19 | 3.15 |
| 6 lb | 3.27 | 2.82 | 2.61 | 2.11 | 3.68 | 3.72 | 2.56 | 3.87 | 2.78 | 3.5 | 3.61 |
| 7 lb | 3.32 | 3.12 | 3.37 | | 3.93 | 3.8 | 3.34 | 4.56 | 3.54 | 3.92 | 4.48 |
| 8 lb | 3.82 | 3.42 | | | 4.03 | 4.08 | 3.54 | 4.61 | 4.28 | 4.42 | 5.17 |
| WEIGHT POSITION | 11 lb NO LOOPS | 11 lb 1 LOOPS | 11 lb 2 LOOPS | 11 lb NO LOOPS | 11 lb NO LOOPS | 11 lb 1 LOOPS | 11 lb 2 LOOPS | 11 lb NO LOOPS | 11 lb 2 LOOPS | 11 lb NO LOOPS | 11 lb NO LOOPS |

FIG.22

FLEXIBLE SURGICAL DEVICE HAVING A ROTATABLE END EFFECTOR ASSEMBLY

This application is a continuation-in-part of U.S. Ser. No. 09/891,775, filed Jun. 25, 2001, which is hereby incorporated by reference herein in its entirety.

BACKGROUND OF THE INVENTION

1. Field of the Invention

This invention relates broadly to surgical devices. In particular, this invention relates to a flexible surgical device having end effectors rotatable about a longitudinal axis of the device. More particularly, this invention relates to a surgical clip applier which is adapted for use through an endoscope and may be used to clamp and/or suture, ducts, vessels, and other tissues, to anchor a tissue, or to attach a foreign body to a tissue.

2. State of the Art

Surgical clips are generally used to apply clamping force to ducts, vessels, and other tissues. In addition, surgical clips are particularly useful in controlling bleeding of a tissue in lieu of suturing or stapling where suturing or stapling is difficult.

All of the currently available surgical multifiring clip appliers are substantially rigid devices intended to extend through a trocar port or through an incision to a surgical site requiring application of a clip. The devices have been rigid because a stiff pushing element has been required in order to exert the required pushing force to move the clip over the tissue.

However, there is a substantial need for a flexible clip applier, particularly one insertable through a lumen of an endoscope. The ability to apply clips through an endoscope would permit myriad minimally invasive surgical solutions to medical problems, especially those of the gastrointestinal tract. However, it is accepted theory that the transmitted force required to advance or form a clip over tissue cannot be produced in the distalmost end of a long flexible device that is commonly constructed with a metal tubular coil, or polymer tube, such as an endoscopic device or catheter. For example, C. Paul Swain, MD, a recognized expert in endoscopic instruments and particularly endoscopic stapling devices, has stated that "[i]t is hard to exert more than 200 g of force on the tissue when pushing. This fact is of course one feature that makes intervention at flexible endoscopy relatively safe". See C. Paul Swain, "What Endoscopic Accessories Do We Really Need?", Emerging Technologies in Gastrointestinal Endoscopy, *Gastrointest. Endosc.*, Vol. 7, No. 2, pp. 313–330 (April 1997). Yet, a pushing force substantially greater than 200 g is required to push a clip over compressed tissue. In fact, it is believed a force in excess of 500 grams (1.1 lbs) is required for a satisfactory instrument, and substantially greater forces, e.g., in excess of 1500 grams (3.3 lbs) would be desirable.

Generally a flexible endoscopic device (e.g., a biopsy forceps device) includes an outer tubular member, typically being constructed of a metal tubular coil or a polymer tube which is poor in transmitting forces that impart tensile stresses to the outer tubular member, a control element longitudinally movable relative to the tubular member, an end effector coupled to the distal ends of both the tubular member and the control element such that relative movement of the control element and the tubular member causes operation of the end effector, and a handle which moves the control element relative to the handle. This type of flexible endoscopic instrument is limited in the amount of pushing force it can generate for several reasons. Compression of a flexible control element (pushing element) tends to cause the pushing element to buckle within the outer flexible sheath of the device. If a relatively larger diameter flexible pushing element is used such that it better resists buckling, the pushing element may impart too much stiffness to the flexing of the endoscopic instrument. In addition, a flexible pushing element of larger diameter is subject to greater frictional forces within the outer sheath which reduces the force transmitted from the handle to the end effector. If the flexible pushing element is made relatively smaller in diameter, it is subject to kinking which will result in little to no force transmitted to the distal end. Kinking is especially a problem in endoscopic instruments, as the endoscope and its lumen may be extended through a tortuous path. For these reasons and others, mechanical application of a relatively large distal end pushing force and particularly clip application have been absent from the capability of flexible endoscopic tools.

SUMMARY OF THE INVENTION

It is therefore an object of the invention to provide a flexible endoscopic device capable of generating a relatively large pushing force at its distal end.

It is another object of the invention to provide an endoscopic clip applier.

It is a further object of the invention to provide a flexible clip applier which can exert a pushing force of at least 500 grams (1.1 lbs), and preferably in excess of 1500 grams (3.3 lbs) via a manually actuatable handle.

It is an additional object of the invention to provide a surgical clip applier which is adapted for use in minimally invasive surgery.

It is also an object of the invention to provide a surgical clip applier which has a pushing element which is not subject to kinking.

It is yet another object of the invention to provide a surgical clip applier which has a pushing element which does not create unsuitably high frictional forces within the outer sheath.

It is still a further object of the invention to provide a surgical clip applier which can store and apply multiple clips.

In accord with these objects, which will be discussed in detail below, a surgical clip applier is provided having a flexible, preferably flat wire wound outer tubular coil, a pair of jaws at the distal end of the tubular coil, a set of end effector wires extending through the outer tubular coil and coupled to the jaws, and a clip-advancing wire extending through the tubular coil. A lubricious, preferably extruded polymer, multilumen barrier sheath extends within the tubular coil and separates the wires from each other and the tubular coil. A clip chamber is provided in the distal end of the tubular coil and stores a plurality of linearly arranged clips. A clip pusher is provided at a distal end of the clip-advancing wire, and adapted to advance the clips in the chamber toward the jaws when the clip-advancing wire is advanced through the barrier sheath and outer tubular coil. The jaws include clamping surfaces which operate to compress tissue between the jaws when the jaws are closed, guides in which a distalmost clip rides distally and is advanced over the clamped tissue when the line of clips is advanced by the clip pusher, and a distal anvil which operates to bend a portion of the distalmost clip to enhance its retention on the clamped tissue. A proximal handle is provided for movement of the clip-advancing wire and end effector wires relative to the barrier sheath to effect (1)

clamping and rotation of the jaws (relative to each other and about the longitudinal axis of the tubular coil), and (2) advancement of the clip-advancing wire to effect distal movement of a clip.

The flat wire wound tubular coil is preferred over round wire (though not necessarily required over a round wire wound tubular coil) because it is flexible, yet sufficiently longitudinally stiff such that the device may be pushed through the lumen of the endoscope. In addition, the flat wire wound tubular coil can be made with a high preload and has a tensile spring constant sufficiently high that it resists buckling and uncoiling during application of a pushing force by the handle against the clip-advancing wire. The clip-advancing wire has a sufficiently large diameter to transmit force, yet small enough to minimize internal friction when moved within a device flexed through a tortuous path in an endoscope. The end effector wires are large enough to handle the high closing force from the handle, and to resist compressive buckling when moved in an opposite direction, yet small enough to be coupled to diminutive jaws. The multilumen barrier sheath supports the clip-advancing wire and end effector wires along their length to reduce compressive buckling, and provides a separation layer to reduce friction. Movement of the clip-advancing wire relative to the outer tubular coil causes a compressive force in the clip-advancing wire and tensile forces in the outer tubular member such that a relative pushing force is transmitted to the distal end of the clip-advancing wire in excess of the perceived threshold of the 200 grams (0.44 lbs). In fact, one embodiment of the device of the invention, sized for endoscopic use, provides a pushing force in excess of 2267 grams (5 lbs).

In operation, the jaws can be moved through a working channel of an endoscope in a closed position. Once exited, the handle can be operated to open the jaws and rotate the jaws to a desired orientation. The jaws are positioned on either side of tissue about which it is desired to place a clip and the handle is operated to pull the end effector wires such that the jaws clamp about the tissue. The handle is then locked to maintain the jaws in the clamped position. The handle is operated to effect advancement of the clip-advancing wire through the tubular coil such that a clip is advanced through the jaw guides and over the tissue. The clip is advanced until a portion thereof is forced against the anvil of the jaws to effect bending of the clip portion such that that portion moves laterally to pierce the clamped tissue. After the clip is applied, the jaws are released from about the tissue, and the end effector assembly may then be moved to another tissue location to apply additional clips.

Additional objects and advantages of the invention will become apparent to those skilled in the art upon reference to the detailed description taken in conjunction with the provided figures.

BRIEF DESCRIPTION OF THE DRAWINGS

FIG. 5 is an enlarged view of the handle of the surgical clip applier with the handle in the same position as shown in FIG. 4;

FIG. 16 is an enlarged partial section view of the handle of the surgical clip applier, showing the clip-advancing lever actuated;

FIG. 19 is a broken partial section side elevation view of the distal end of the clip applier according to the invention, shown with the jaws in an open configuration, the formed clip released, and the retainer of a subsequent clip protruding between the jaws;

FIG. 20 is a longitudinal section view of the distal end of the clip applier according to the invention, shown with the jaws in an open configuration and the retainer retracted relative to the view of FIG. 19;

FIG. 22 is a table listing dimensions for the tubular coil, clip-advancing wire, and end effector wires of six prototypes, and the resultant output force achieved with the prototype.

DETAILED DESCRIPTION OF THE PREFERRED EMBODIMENTS

Figure 1:
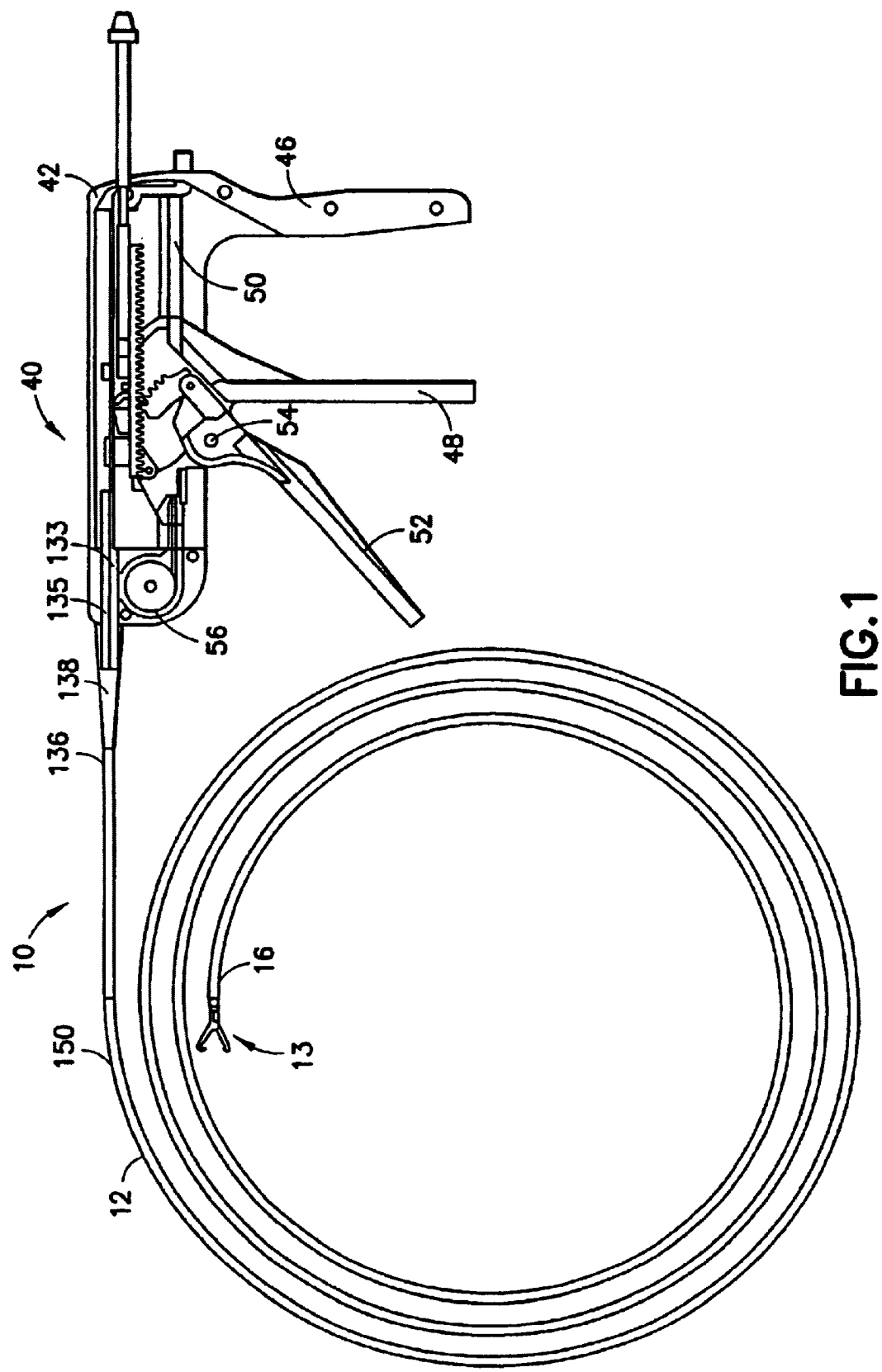
FIG. 1 is a partial section side elevation view of a surgical clip applier according to the invention, shown with the handle configured to provide the jaws in an open configuration.

Turning now to FIGS. 1, 2, 2A and 3, a flexible clip applier 10 suitable for insertion through a working channel (lumen) of an endoscope is shown. The clip applier 10 generally includes a flexible, flat wire wound outer tubular coil 12 having an end effector assembly 13 mounted at a distal end 16 thereof. The end effector assembly 13 includes a clevis (jaw mount) 14 rotatably supporting a pair of jaws 18, 20. End effector wires 22, 24 extend through the tubular coil 12 and have distal ends 26 respectively coupled to the jaws 18, 20. A clip-advancing wire 30 extends through the tubular coil 12 and includes a distal end 32 provided with a clip pusher 34. A lubricious, preferably extruded, multilumen barrier sheath 36 extends through substantially the entire length of the outer tubular coil 12 and separates the end effector wires 22, 24 and clip-advancing wire 30 from each other and the outer tubular coil 12. A proximal handle assembly 40 is provided for moving the end effector wires 22, 24 and clip-advancing wire 30 relative to the tubular coil 12 to effect clamping and rotation of the jaws and advancement of a clip, as described in detail below.

Figure 4:
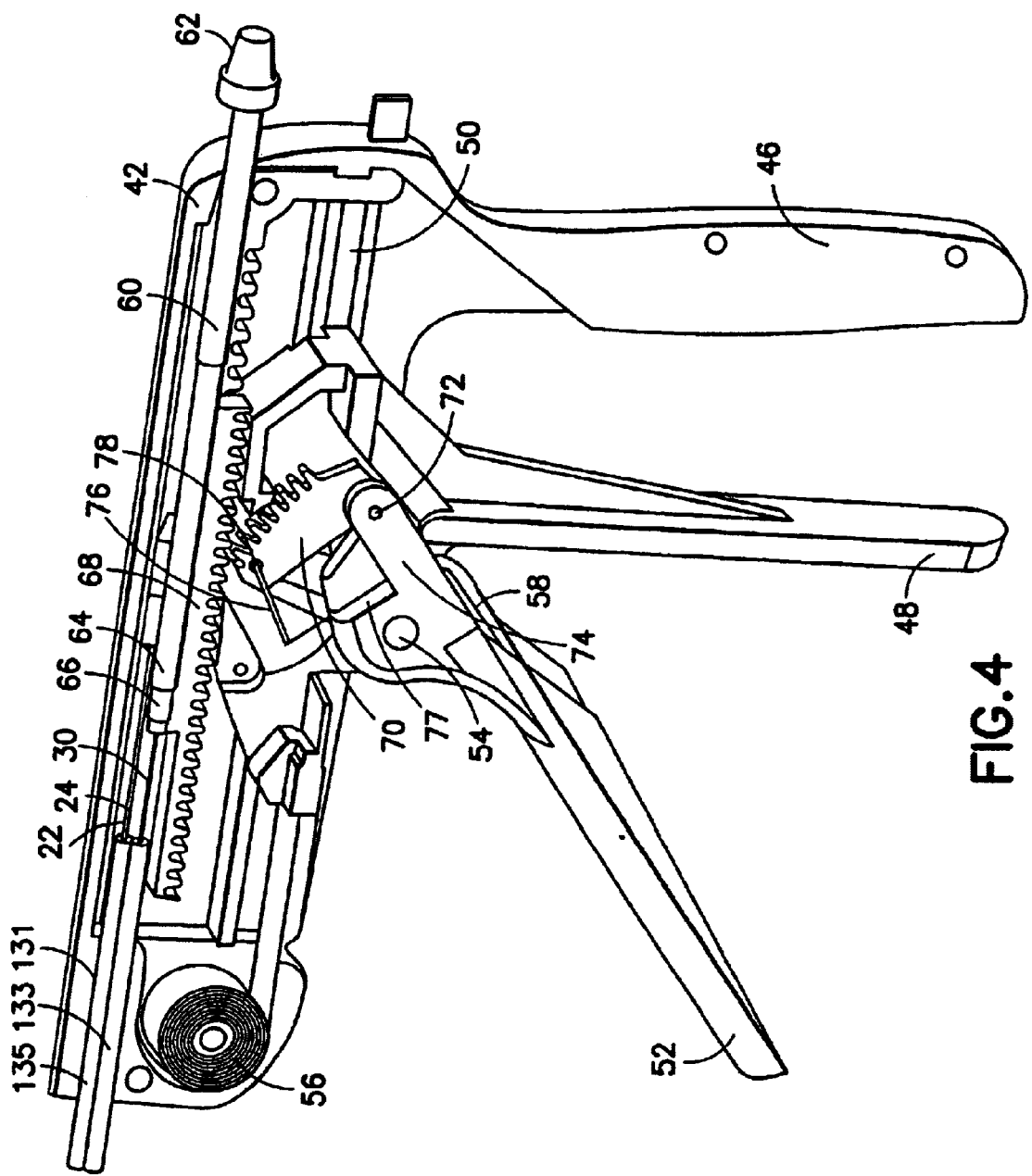
FIG. 4 is a partial section side elevation view of a surgical clip applier according to the invention, showing the right side of the handle positioned to place the jaws in an unloaded closed configuration.
Figure 7:
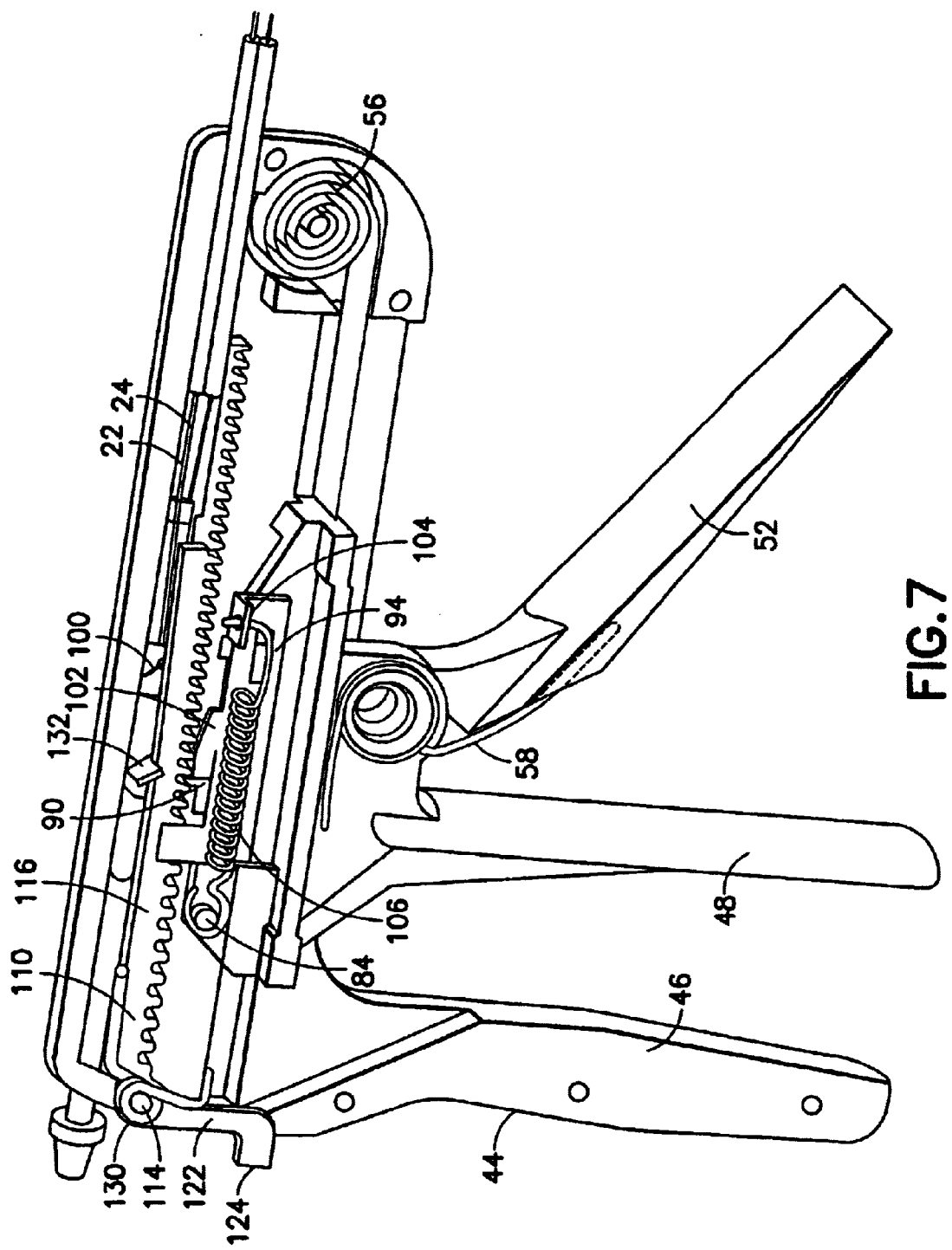
FIG. 7 is a view similar to FIG. 6 with the addition of the various springs.

Referring to FIGS. 4 and 5, more particularly, the handle assembly 40 includes a housing defined by two shell portions 42, 44, a stationary handle 46, a jaw closing lever 48 linearly movable within a slot 50 in the housing and relative to the stationary handle 46, and a clip-advancing lever 52 rotatably mounted on the jaw closing lever 48 with a pivot pin 54. The jaw closing lever 48 is coupled to the end effector wires 22, 24, as described in detail below. The jaw closing lever 48 is biased into an open position (away from the stationary handle 46) with a constant force spring 56 held in a distal portion of the housing such that the jaws 18, 20 are in an open configuration when no manual force is applied against the force of the spring 56 to move the jaw closing lever toward the stationary handle. The clip-advancing lever 52 is forced into an open position, also away from the stationary handle 46, with a torsion spring 58 (FIGS. 4 and 7). The clip-advancing lever 52 is coupled to the clip-advancing wire 30, as discussed in detail below, with rotation of the clip-advancing lever 52 operating to move the clip pusher 34 at the distal end 32 of the clip-advancing wire 30 longitudinally within the tubular coil.

A tube 60 extends from the interior of the handle 40 to the exterior and includes a proximal rotation knob 62. The proximal end of the clip-advancing wire 30 is clamped, or otherwise held, within the tube 60 such that rotation of the knob 62 causes rotation of the entire clip-advancing wire. A distal end 64 of the tube 60 is rotatably coupled within a collar 66. The collar 66 is fixedly coupled to a rack 68. Linear movement of the rack 68 within the housing causes the tube to move longitudinally within and outside of the housing.

Figure 4A:
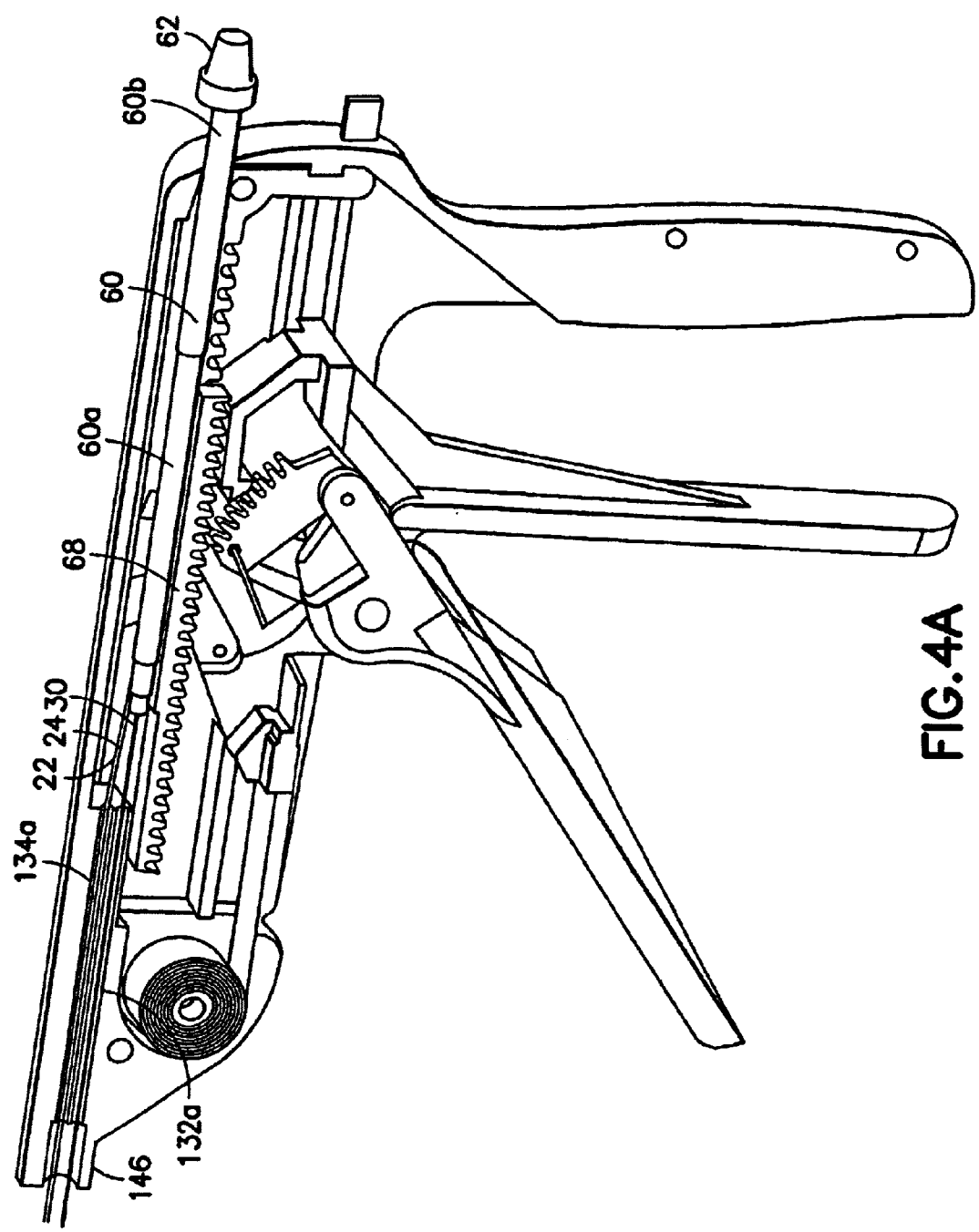
FIG. 4A is a view similar to FIG. 4, illustrating alternative embodiments to the handle of the clip applier according to the invention.

Alternatively, referring to FIG. 4A, the tube 60 may be telescoping, having two rotationally interfering sections 60a and 60b, such that movement of the rack 68 moves a distal section 60a of the tube relative to a proximal section 60b, thereby maintaining a constant length for extension of the proximal section 60b of the tube outside the housing. The rotationally interfering portions, e.g., each having a hex shape, permit rotationally forces to be transmitted from the knob 62 to the distal end 64 of the tube.

Referring back to FIG. 4, a pinion 70 is rotatably mounted at 72 to an upper portion 74 of the clip-advancing lever 52 and positioned to act on the rack 68 when the clip-advancing lever is rotated. As such, when the clip-advancing lever 52 is rotated about pivot 54 toward the jaw closing lever 48, the rack 68 and the clip-advancing wire 30 are advanced. The rack 68 is preferably substantially longer than what is required by the number of teeth on the pinion 70. As a result, the pinion 70 can act upon the rack 68 in any location at which the jaw closing lever 48 may be positioned upon closing the jaws 18, 20. This, when the jaw closing lever 48 is pulled back toward the stationary handle 46 to effect closure of the jaws 18, 20 about tissue, the jaw closing lever 48 may be located at a location which is consistent with the thickness and consistency of the tissue about which the jaws are to be closed.

The teeth of the pinion 70 are preferably at a positive engagement angle relative to the teeth of the rack 68 because of the location of the pinion pivot axis 72. Then, when the pinion is rotated, the rack is moved longitudinally. A leaf spring 76 acts between the pinion 70, at hole 78, and the advancing lever 52 at shelf 77 to force the pinion 70 into the rack 68. After firing a clip, as discussed below, release of the clip-advancing lever 52 allows the spring 58 to return the lever 52 back to its unbiased position, and the pinion 70 rotates about the pinion axis 72 against the leaf spring 76 and over the rack 68.

Figure 6:
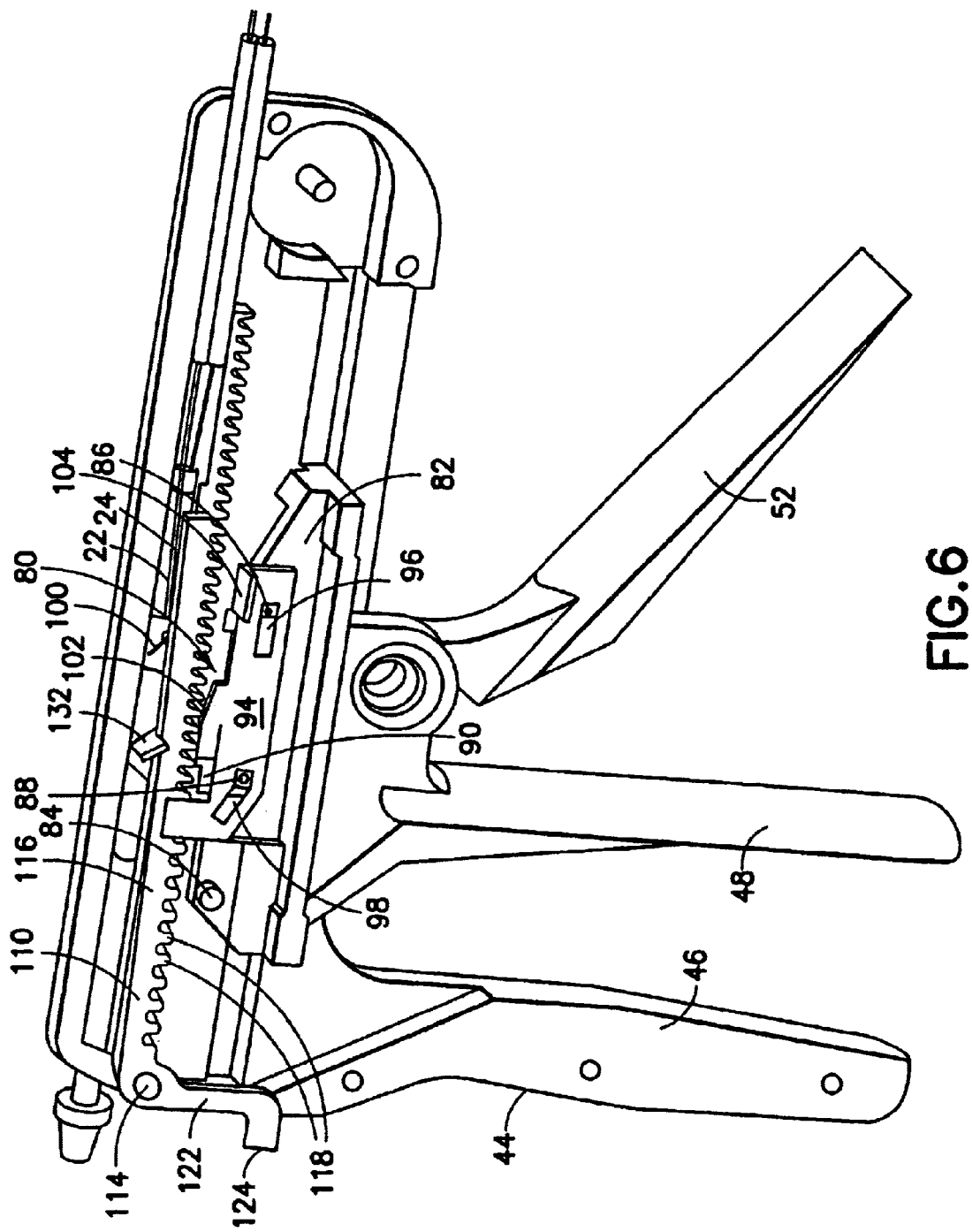
FIG. 6 is a view similar to FIG. 4 of the left side of the handle.
Figure 8:
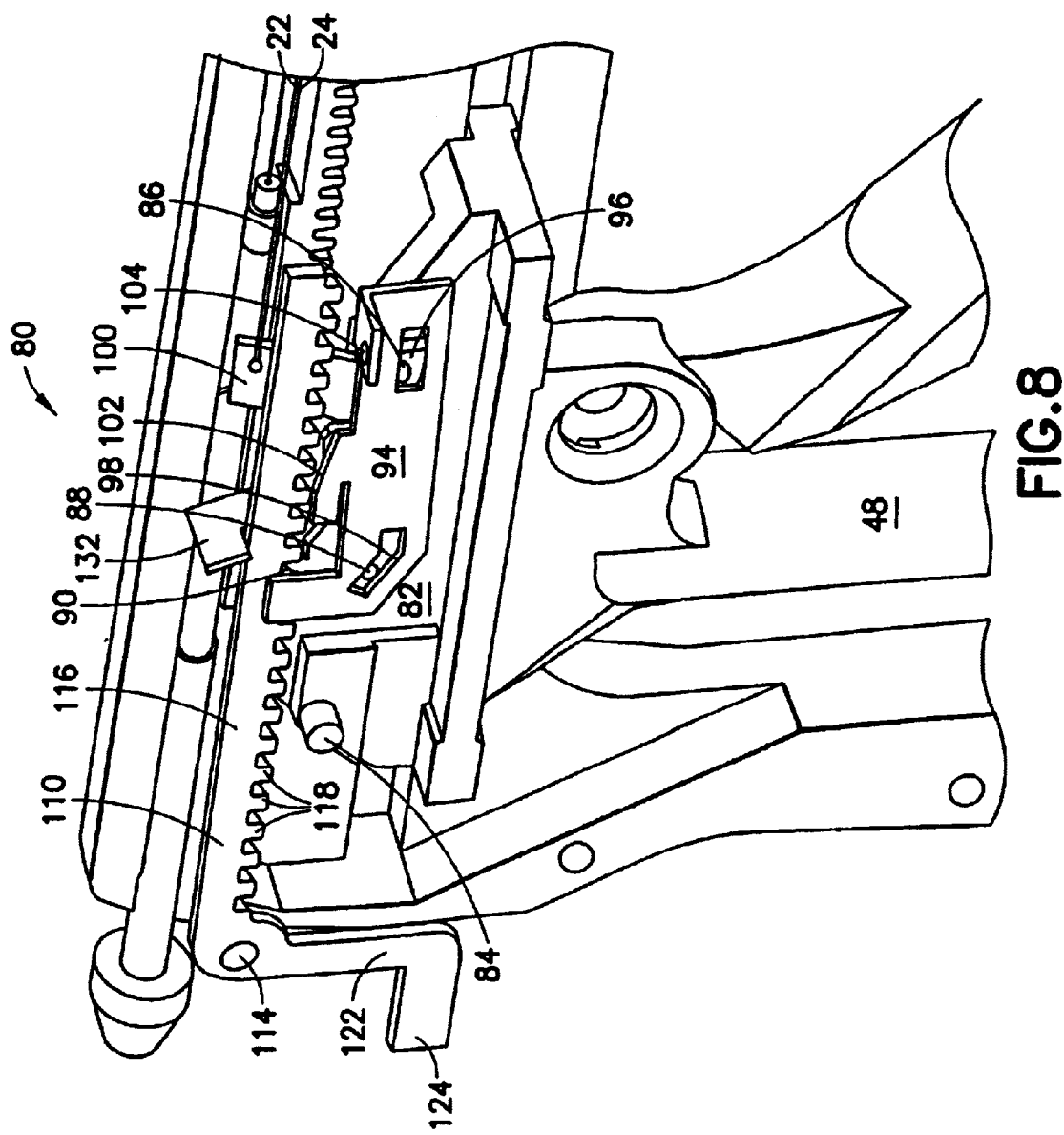
FIG. 8 is an enlarged broken section view of the proximal left side of the handle of the clip applier according to the invention.

Turning now to FIGS. 6 through 8, the jaw closing lever 48 includes a spring activated catch system 80 which locks the jaw closing lever when a predetermined load is applied thereto rather than when the closing lever is located at any particular location. The catch system 80 includes the following structures on an upper mount portion 82 of the jaw closing lever 48: a proximal spring mount 84; two spaced apart bolts 86, 88; and a locking tooth 90. The locking tooth 90 includes a proximal cam 92. The catch system 80 further includes the following additional structures: a latch 94 having a linear slot 96 and a cam slot 98, which are positioned over bolts 86, 88 respectively; an end effector wire mount 100 to which the proximal ends of the end effector wires 22, 24 are attached; an upper cam surface 102 for the below-described lever lock 110; and a spring catch 104. An extension spring 106 (FIG. 7) is held between the spring mount 84 and spring catch 104. A generally L-shaped lever lock 110 is rotatably coupled about a lever pivot 114 formed at the proximal end of the handle. An elongate portion 116 of the lock 110 includes a comb; i.e., the portion 116 includes a plurality of teeth 118, each of which include a distal camming surface 120. Another portion 122 of the lever lock 110 is provided with a release button 124 which extends outside of the handle housing. A torsion spring 130 is provided about the pivot 114 to bias the lever lock 110 down toward the locking tooth 90. A safety 132 is also provided to prevent release of the jaw closing lever 48 when the clip-advancing lever 52 is moved from an unbiased position, thereby preventing inadvertent release of unapplied clips.

Once the jaws are closed about tissue, as discussed further below, it is desired to maintain their closed position until a clip is advanced over the tissue. In view of this object, the catch system 80 function as follows. Still referring to FIGS. 6 through 8, the cam surface 102 is generally adapted to position the teeth 118 of the lever lock 110 located in front of the locking tooth 90 above the locking tooth, such that the jaw closing lever 48 may be moved linearly. When the jaw closing lever 48 is moved toward the stationary lever 46, tension is increased in the end effector wires 22, 24 to move the jaws 18, 20 from an open position to a closed position. As the tension increases in the end effector wires 22, 24 and exceeds the tension of the extension spring 106, the latch 94 moves distally relative to the jaw closing lever 48. Then, movement of the jaw closing lever 48 relative to the latch 94 causes the bolts 86, 88 to ride within the linear slot 96 and the camming slot 98, respectively. Referring to FIG. 8, movement of bolt 88 within camming slot 98 forces the proximal end of the latch 94 downward and permits the lever lock 110 to rotate clockwise. This causes the locking tooth 90 to engage the toothed portion 116 of the lever lock 110 and lock the position of the jaw closing lever 48. The load applied to the end effector wires is then limited to the force applied by the extension spring 106 (FIG. 7). The jaw closing lever 48 then may be released by pushing the release button 124 sufficiently to rotate the lever lock 110 against the bias of the torsion spring 130 and clear the locking tooth 90.

Turning now to FIGS. 1, 2, 4 and 6, the distal end of the housing 42, 44 of the handle assembly 40 includes a slot 131 in which two preferably substantially rigid and preferably low friction tubes 133, 135, e.g., brass tubes, are provided. The proximal end 136 of the tubular coil 12 is coupled to the housing in alignment with the tubes 133, 135 with a flare nut coupling 138 or an equivalent assembly. The clip-advancing wire 30 extends from the rotation tube 60 through tube 133 and into a clip-advancing wire lumen 140 of the barrier sheath 36. The clip-advancing wire 30 extends therethrough to the distal end 16 of the tubular coil 12. The end effector wires 22, 24 extend from end effector wire mount 100 through tube 135 and into respective end effector wire lumina 142, 144 of the barrier sheath 36, and then extend therethrough to the distal end of the tubular coil. Wires 22, 24 and 30 are provided in separate lumina within the barrier sheath 36 in order to minimize friction between the wires and reduce buckling and kinking of the wires along the length of the tubular coil 12.

Turning again to FIG. 4A, rather than using tubes to direct the wires from the housing into the barrier sheath in tubular coil, the housing may be formed with channels which provide the same function. For example, channels 132a, 132b are adapted to direct the clip-advancing wire 30 and end effector wires 22, 24, respectively, into the barrier sheath 36 within the tubular coil 12. In addition, the housing may be formed with distal structure, e.g., a cylindrical protrusion 146, facilitating the coupling of a flare nut assembly thereto.

Referring back to FIG. 2, the tubular coil 12 is a preferably stainless steel (or other metal or metal alloy) flat wire wound wire tubular coil, though a round wire wound tubular coil may be used. The tubular coil 12 is fairly stiff such that the device can be pushed through the endoscope to the treatment area. The tubular coil 12 has a spring constant sufficiently high in order to resist uncoiling when subject to the tensile load created when the handle applies a pushing force to the clip-advancing wire and the clips, as discussed in more detail below, and minimize buckling during force transmission. In addition, the tubular coil 12 is preloaded such that each turn is substantially in contact with the adjacent turns 360° around the tubular coil. The outer diameter of the tubular coil 12 has an outer diameter smaller than the inner diameter of the working channel (lumen) of an endoscope for which it is intended, and the inner diameter of the tubular coil should be maximized so that it may readily accept the barrier sheath, and clip-advancing wire and end effector wires, as well as form a chamber for a plurality of clips, as discussed below. In preferred embodiments, the tubular coil 12 of a device adapted for an endoscope having a 3.2 mm working channel has an outer diameter preferably not exceeding approximately 3.175 mm (0.125 inch), and a preferably an inner diameter of at least approximately 0.90 mm (0.035 inch) so that it may accept the end effector wires 22, 24, clip-advancing wire 30, barrier sheath 36, and clips 202. The tubular coil inner diameter preferably corresponds to the transverse dimension of a clip 202, discussed below, so that the clip is stably directed through the chamber 200. The wire of the tubular coil 12 has a width W preferably between approximately 0.635 mm to 1.270 mm (0.025 inch to 0.050 inch), and a thickness T preferably at least approximately 0.13 mm to 0.75 mm (0.005 inch to 0.030 inch). The tubular coil length should at least be the length of the endoscope working channel, generally 150 cm to 250 cm. A substantial length of the tubular coil 12 is preferably covered in a high density polyethylene (HDPE) sheath 150 (FIGS. 1, 2 and 2A).

The barrier sheath 36 within the tubular coil is preferably non-circular in shape to reduce contact points and thereby minimize friction between the barrier sheath and the tubular coil. The primary purpose of the sheath is to maintain a close fitting bearing surface for the clip-advancing wire, although its three distinct lumina help reduce friction between all the wires. The sheath 36 preferably free floats within the tubular coil; i.e., it is not attached to the tubular coil at its ends or along its length. Preferred cross-sectional shapes include generally rectangular and triangular (each with or without broken or rounded edges) and trefoil. The barrier sheath 36 is preferably an extrusion made from polypropylene, an FEP fluoropolymer resin (FEP), polytetrafluoroethylene (PTFE), high density polyethylene (HDPE), nitrol polyvinyl chloride, nylon, or any other lubricious polymer.

The clip-advancing wire 30 is preferably made of nickel-titanium alloy (NiTi) or stainless steel. The NiTi construction permits the clip-advancing wire 30 to transmit torque (by rotation of the rotation knob 62) without taking a cast, and with minimal whipping. The clip-advancing wire 30 has a sufficiently large diameter to transmit force, yet not so large that it is prevented from functioning through a tortuous path or fit within the tubular coil 12. A preferred diameter for the clip-advancing wire is approximately 0.375 mm to 0.89 mm (0.015 inch to 0.035 inch).

Figure 2:
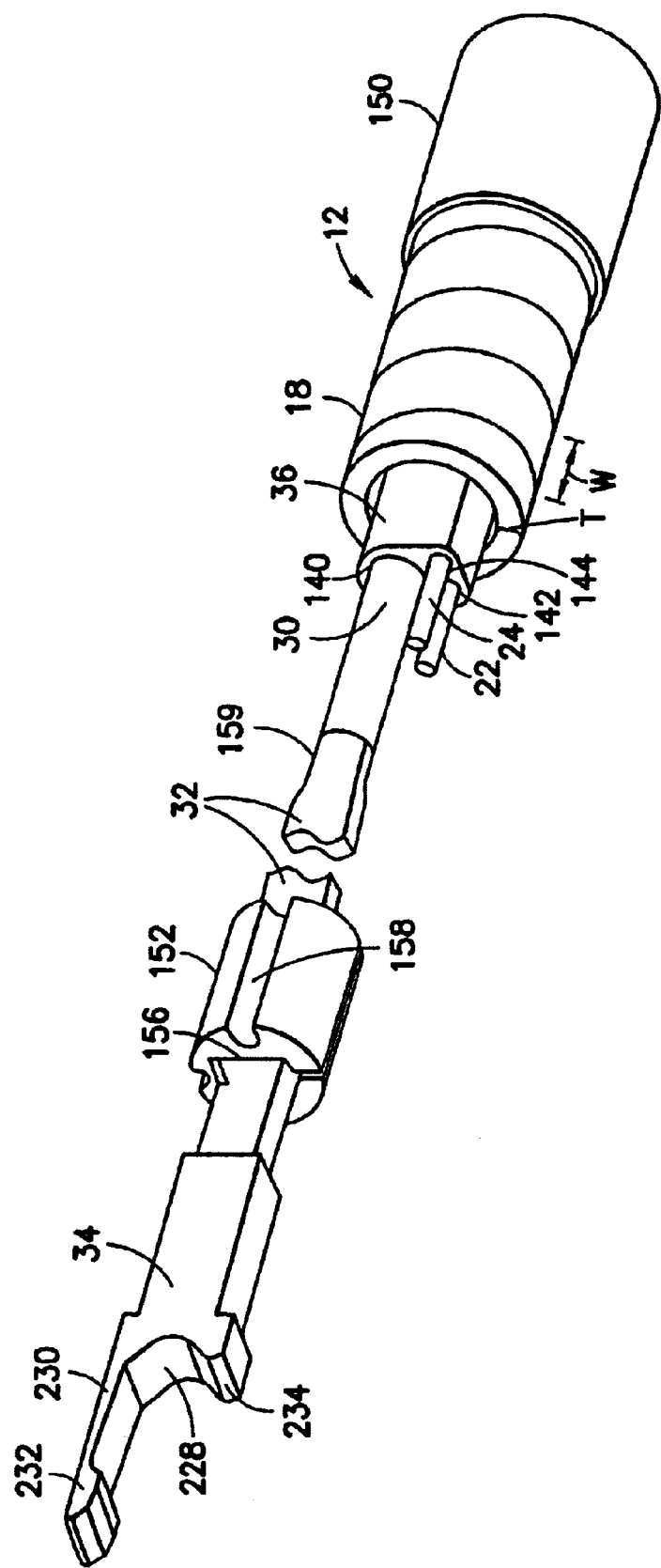
FIG. 2 is a broken perspective view of a distal portion of the clip applier according to the invention.
Figure 2A:
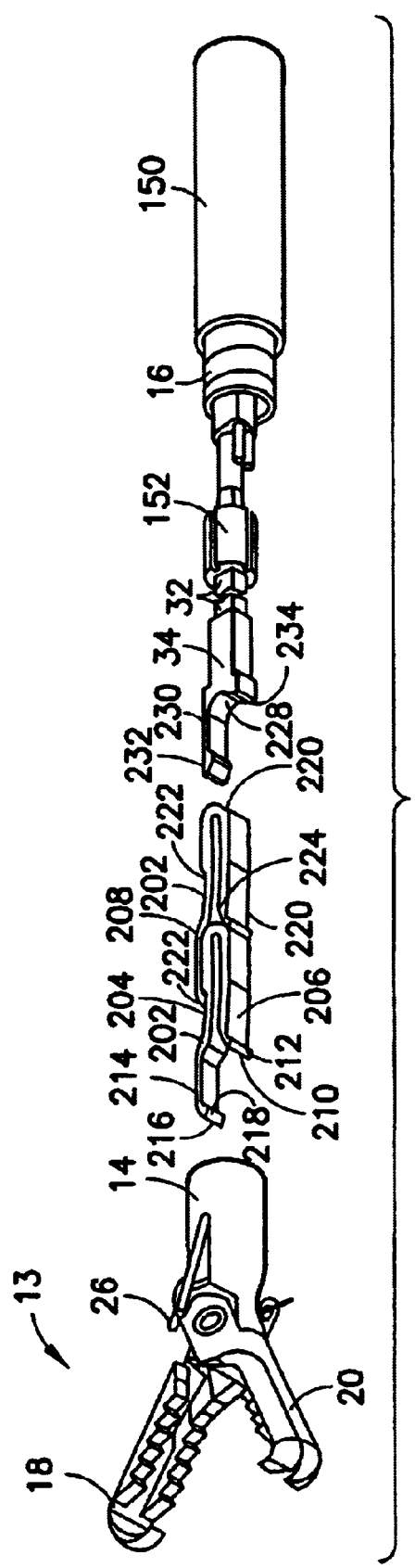
FIG. 2A is an exploded and broken perspective view of a distal portion of the clip applier according to the invention.
Figure 3:
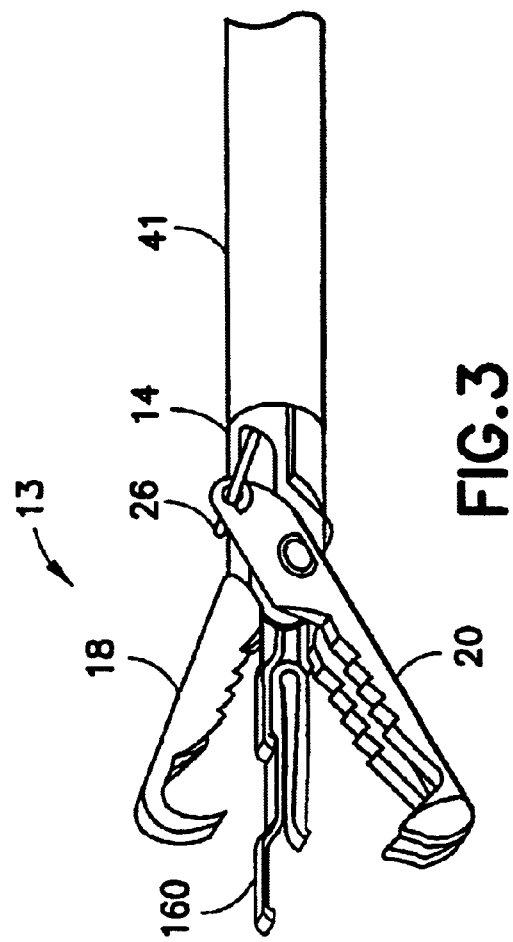
FIG. 3 is a perspective view of the jaw assembly of the clip applier according to the invention, and a clip.
Figure 2B:
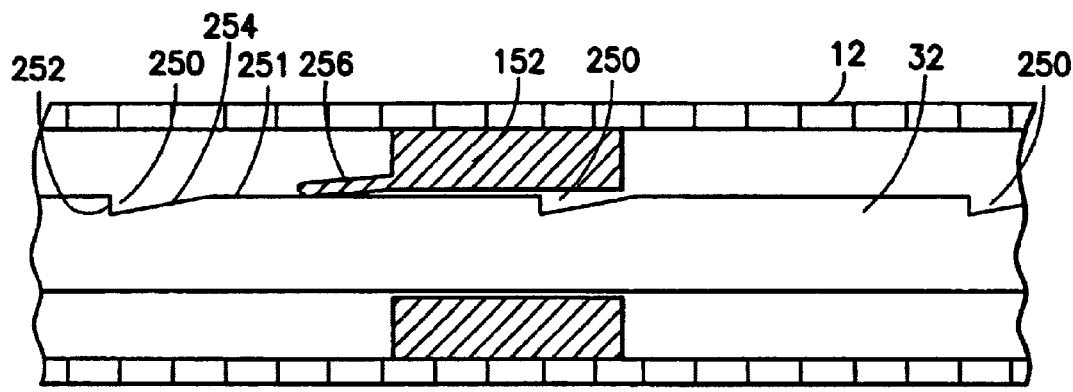
FIG. 2B is a broken schematic view of a distal end of the clip-advancing wire and the coil connector.

Referring to FIGS. 2, 2A and 2B, the distal end 32 of the clip-advancing wire 30 has a non-circular cross-section, and is preferably rectangular in shape. The distal end 32 is preferably a length four to five times the length of the clip pusher 34. A coil connector 152 is coupled within the distal portion 16 of the tubular coil 12, e.g., by welding, press fitting, interference fit, pinning, etc., preferably approximately 25 mm to 50 mm from the distal end of the tubular coil (i.e., the length of a linear arrangement of five or so clips), and includes a central keyhole 156 having a non-circular cross section, and two end effector channels 158 (only one shown) through which the end effector wires 22, 24 extend. The distal end 32 of the clip-advancing wire 30 can be longitudinally moved through the keyhole 156, with the transition 159 of the clip-advancing wire 30 from non-circular to circular outer shape functioning as a stop against the keyhole 156 for additional distal movement.

Figure 2C:
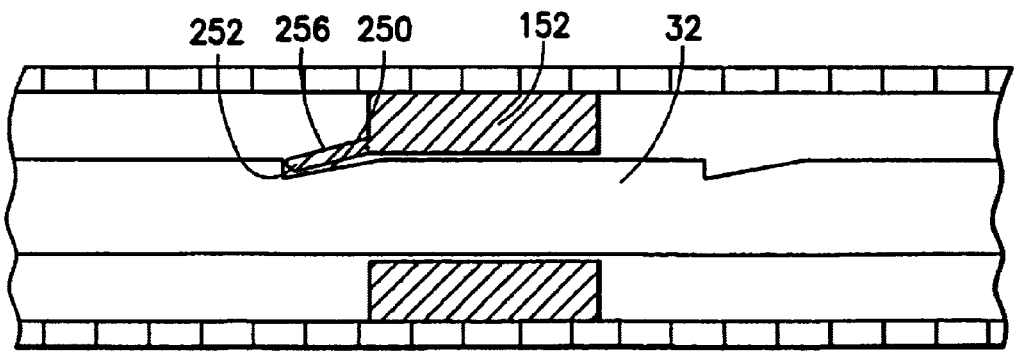
FIG. 2C is a broken schematic view of a distal end of the clip-advancing wire and the coil connector illustrating the limitation on proximal movement of the clip-advancing wire relative to the coil connector.

Referring to FIG. 2B, the distal end 32 of the clip-advancing wire 30 also includes notches 250 along one side 251 of the distal end 32 which have a distal surface 252 substantially perpendicular to the side 251 and proximal beveled surface 254. The coil connector 152 includes a resilient catch 256 in alignment with the notches 250. When the clip-advancing wire 30 is moved distally through the keyhole 156, the beveled surface 254 of the notches 250 rides against the catch 256, bending the catch for clearance. However, as distal surface 252 interferes with the catch 256 when the clip-advancing wire 30 is moved proximally relative to the coil connector 152, the clip-advancing wire 30 may not be moved proximally by a distance which would cause a notch 250 to pass the catch 256 (FIG. 2C).

Moreover, rotation of the clip-advancing wire 30 causes a rotational moment to be applied to the connector 152 and consequently the distal end of the tubular coil 12. The distal end of the preloaded tubular coil 12 can be thereby rotated 360° in each of the clockwise and counterclockwise directions by rotation of the rotation knob 62 attached to the proximal end of the clip-advancing wire 30. Because the end effector assembly 13 is attached to the distal end of the tubular coil, rotation of knob 62 effects rotation of the end effector assembly 13 and the jaws 18, 20.

The end effector wires 22, 24 are large enough in diameter to preferably handle up to fifteen pounds of closing force from the handle assembly and also to handle the force required to open the jaws 18, 20 without buckling. However, the end effector wires must be small enough in diameter to attach to the jaws, and fit in the tubular coil 12. A preferred diameter for the end effector wires is approximately 0.178 mm to 0.375 mm (0.007 inch to 0.015 inch), though other sizes may be used.

Figure 9:
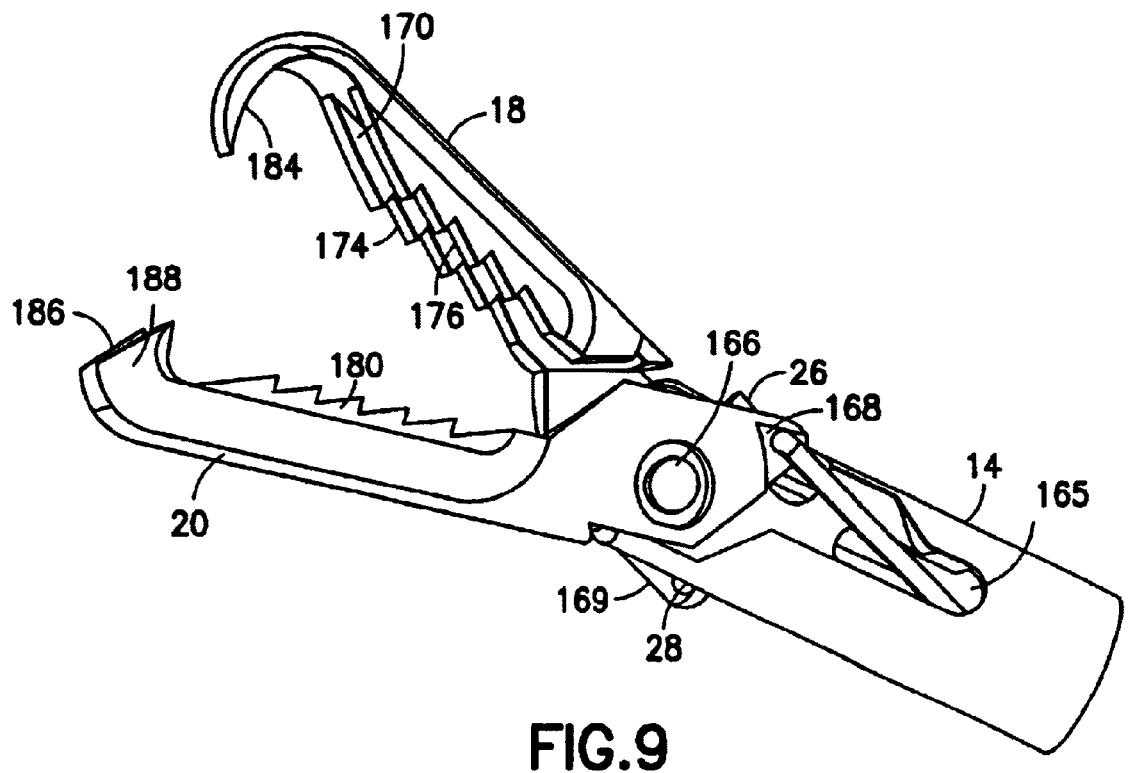
FIG. 9 is an enlarged side perspective view of the end effector assembly.
Figure 10:
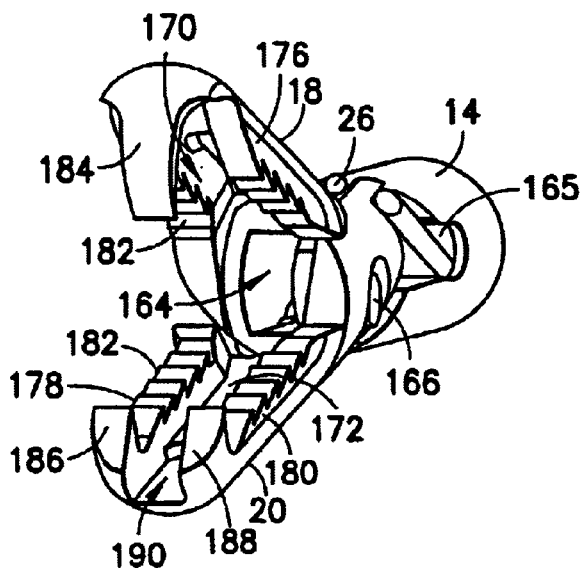
FIG. 10 is an enlarged distal end perspective view of the end effector assembly.

Referring to FIGS. 9 and 10, the clevis 14 of the end effector assembly 13 is preferably coupled directly to the distal end of the tubular coil 12. The clevis 14 includes a central clip channel 164 having a preferably rectangular cross section, and two lateral openings 165 through which the distal ends of the end effector wires 26, 28 can respectively exit. The jaws 18, 20 are each rotatably coupled about the clevis 14 with a respective axle 166 (one shown) which does not interfere with the channel 164. Each jaw 18, 20 includes a proximal tang 168, 169 respectively, which is coupled to the distal ends of the respective end effector wires 26, 28. The distal portion of each jaw 18, 20 includes a clip guide 170, 172, respectively, and clamping surfaces 174, 176 on jaw 18, and clamping surfaces 178, 180 on jaw 20 extending along each side of the guide 172. All of the clamping surfaces 174, 176, 178, 180 preferably have proximally directed teeth 182 which pulls target tissue toward the clip channel 164 as the jaws are closed, and also securely grips the tissue when a clip is advanced thereover. The distal end of jaw 18 includes an anvil 184 which is in alignment with the clip guide 170 which curves (or is angled) toward jaw 20. Jaw 20 includes two distal anvil guides 186, 188 between which the anvil 184 is positioned when the jaws are moved to a closed position. Jaw 20 also defines a distal well 190 between the anvil guides 186, 188 which is lower than the surface of clip guide 172.

Figure 11:
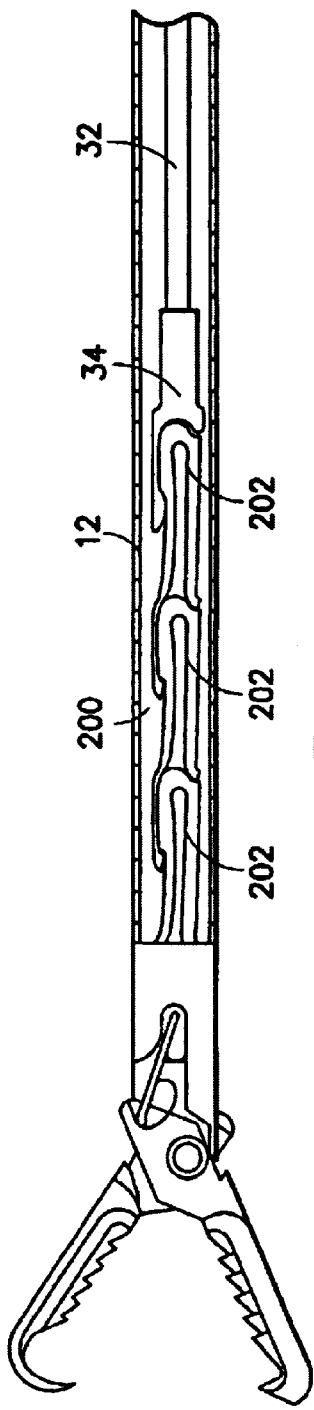
FIG. 11 is a broken partial section side elevation view of the distal end of the clip applier according to the invention.

Referring to FIG. 11, a clip chamber 200 for storing a plurality of linearly arranged clips 202 (FIG. 2A), described further below, is formed between the coil connector 152 (FIGS. 2 and 2A) and the distal end 16 of the tubular coil 12. The clip chamber 200 extends into the clip channel 164 of the clevis 14. The clip pusher 34 is provided at the proximal end of the chamber and situated to push on a proximalmost clip such that all clips in front of the clip pusher 34 are advanced toward the jaws 18, 20 when the clip-advancing lever 52 is actuated to cause the clip-advancing wire 30 to move distally relative to the tubular coil 12.

The clip pusher 34, preferably made of stainless steel, is coupled to the distal end 32 of the clip-advancing wire 30, e.g., by mechanical joining or welding. The clip pusher 34, as described in more detail below, is provided with a shape substantially similar to the distal portion of a clip 202 (FIG. 2A) adapted to be used in the clip applier. Such clips 202 are described in detail in previously incorporated U.S. Ser. No. 09/891,775. Generally, referring to FIG. 2A, the clips 202 are each in a generally U-shaped configuration with first and second arms 204, 206, and a bridge portion 208 therebetween. The first arm 204 extends into a deformable retainer 214 preferably having a tissue-piercing end 216 and preferably also a hook 218, and the second arm 206 is provided with a tip 210 preferably having one or more catches 212. The clip 202 is provided with structure that facilitates the stacking (or chaining) of a plurality of clips in the clip chamber 200. The structure includes: a notch 220 at a junction of the second arm 206 and the bridge portion 208 which is adapted to receive the tip 210 of the second arm 206 of another clip; an elongate recess 222 along the exterior of the first arm 204 which is adapted to receive the retainer 214 of the first arm of another clip; and an interior configuration 224 at the ends of the first and second arms which corresponds to an exterior shape of the proximal bridge portion 208 of another clip. In one embodiment, the clips 202 are each approximately 6.86 mm (0.27 inch) in length from the bridge 208 to the end of the retainer 214, have a width of approximately 0.90 mm (0.035 inch), and a height of 1.80 mm (0.070 inch). However, it is understood that the clip dimensions may be adapted for use in devices having tubular coil inner diameters of various sizes.

Referring to FIGS. 2 and 2A, the clip pusher 34 includes a rear clip seat 228 which corresponds to the exterior shape of the proximal end of the clip. The clip pusher 34 also includes a distally extending arm 230 having a distal clip catch 232 (adapted to seat in the recess 222 of clip 202), and a shoulder 234 adjacent the clip seat 228 on the side opposite the arm 230. As such, the clip pusher 34 includes structure which is adapted to conform the proximal end of a clip 202 for transferring a pushing force relative to the tubular coil. In addition, the clip catch 232, by engaging in the recess 222 of a clip 202, prevents clips from unintentionally moving distally. The clip catch also permits moving a clip 202 proximally, by retracting the clip pusher 34 such that the clip catch 232 forces back against wall at the rear of the recess 222 and pulls the engaged clip proximally, which in turn moves other clips in the 'chain'. The operation of the distal portion of the device 10 (including the end effector assembly 13, the clip pusher 34, and the clip chamber 200) will become evident with reference to the following description of the use of the device 10.

Figure 12:
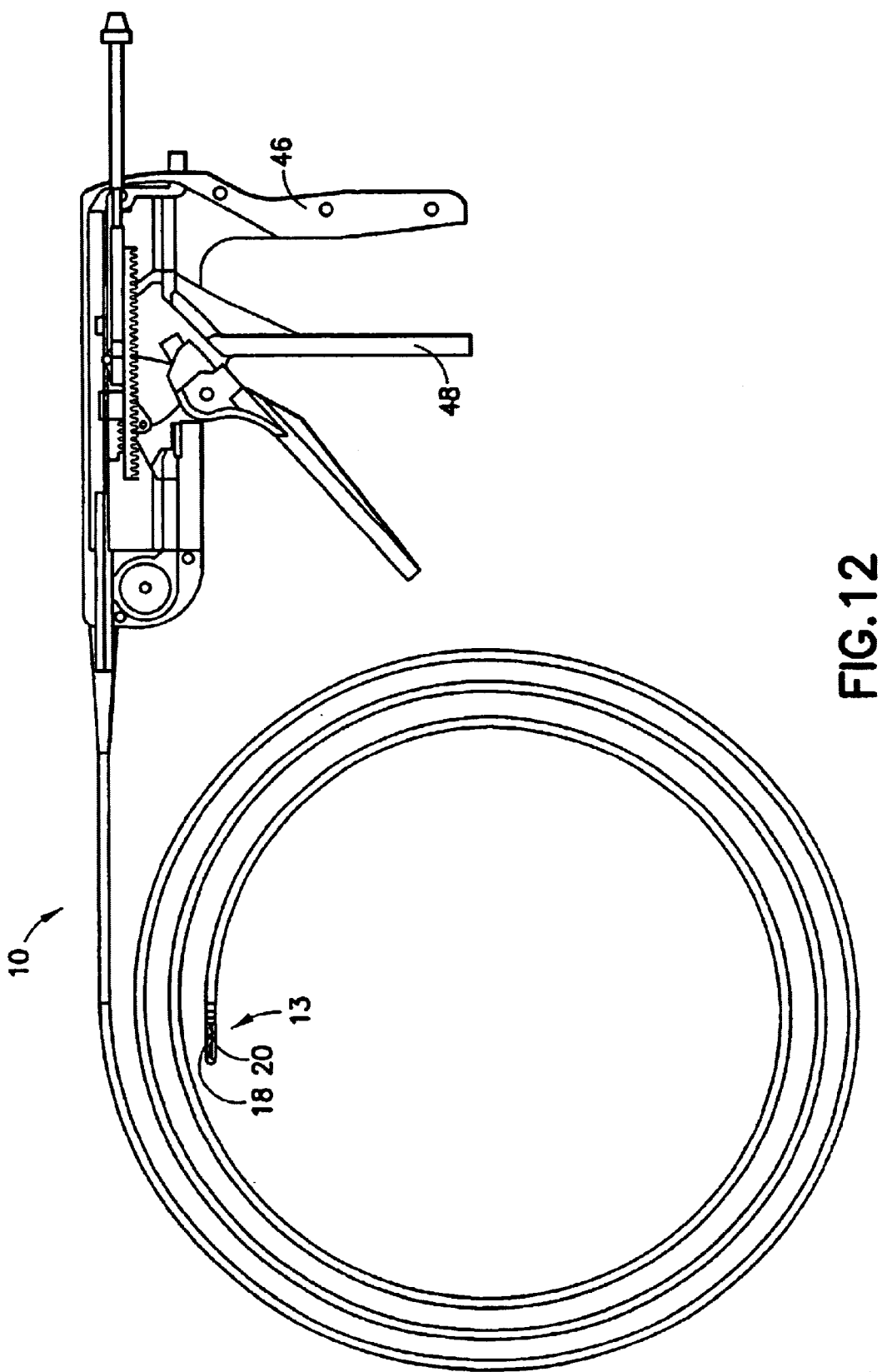
FIG. 12 is a view similar to FIG. 1, showing the handle configured such that the jaws are in a unloaded closed position, and shown without the pinion on the jaw closing lever.
Figure 13:
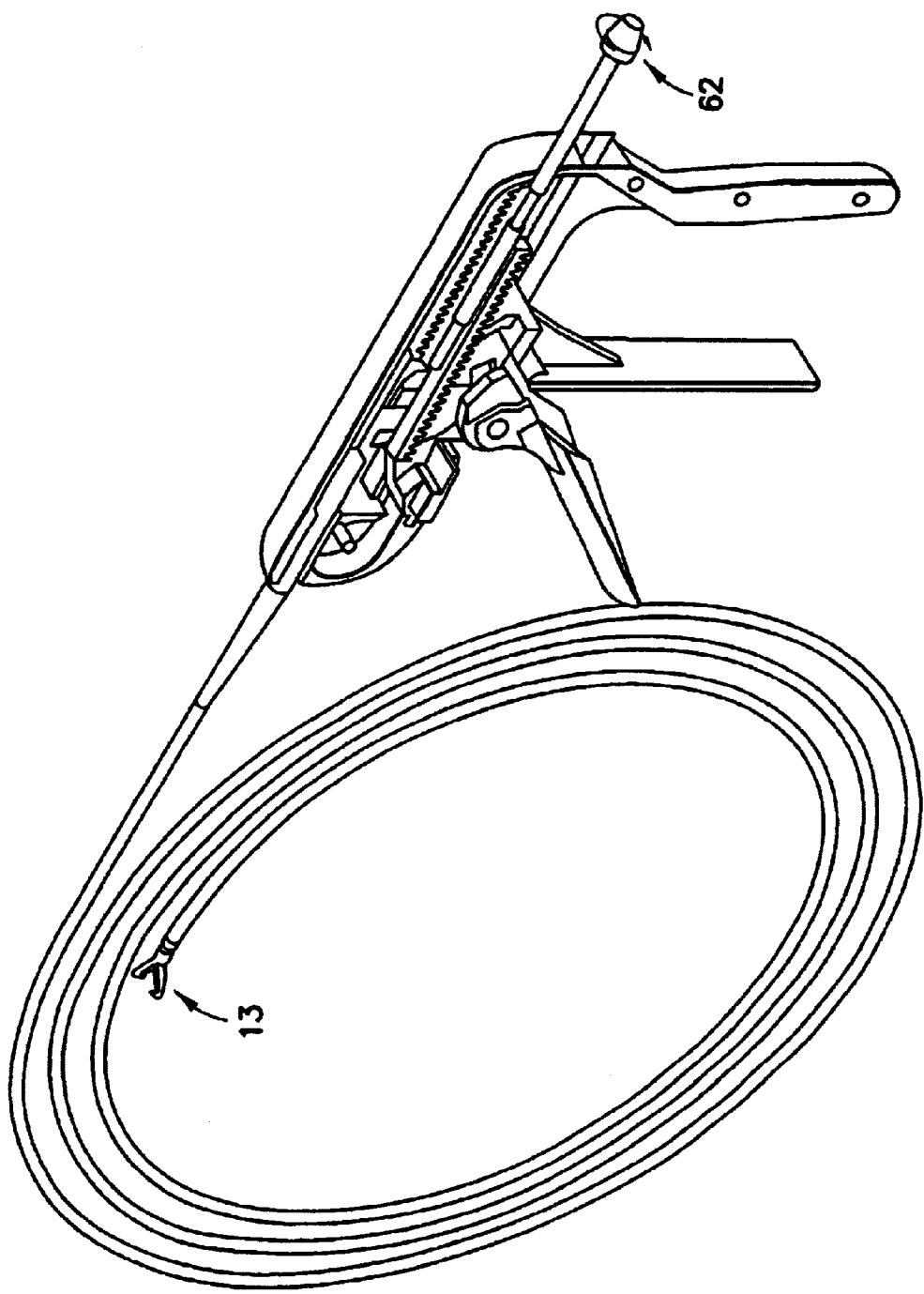
FIG. 13 is a partial section perspective view of a surgical clip applier according to the invention, illustrating rotation of the end effector assembly by operation of the rotation knob.

Referring to FIGS. 4 and 12, the jaw closing lever 48 is moved toward the stationary handle 46, against the bias of spring 56, to cause the jaws 18, 20 of the end effector 13 to move into a closed position. Movement of the lever 48 adapts, in size, the distal end of the device for delivery through the lumen (working channel) of an endoscope, but preferably does not substantially load the end effector wires 22, 24. Once the end effector assembly 13 has exited the distal end of the endoscope, the jaw closing lever 48 can be released to open the jaws (FIG. 1). Referring now to FIG. 13, the proximal rotation knob 62 can be rotated which, as discussed above, effects rotation of the entire clip-advancing wire 30 and, hence, rotation of the end effector assembly 13. Briefly, this is because the end effector assembly 13 is coupled to the tubular coil 12 and the tubular coil is provided with a fixed coil connector 152 which is rotated by rotation of the distal end 32 of the clip-advancing wire 30.

Figure 14:
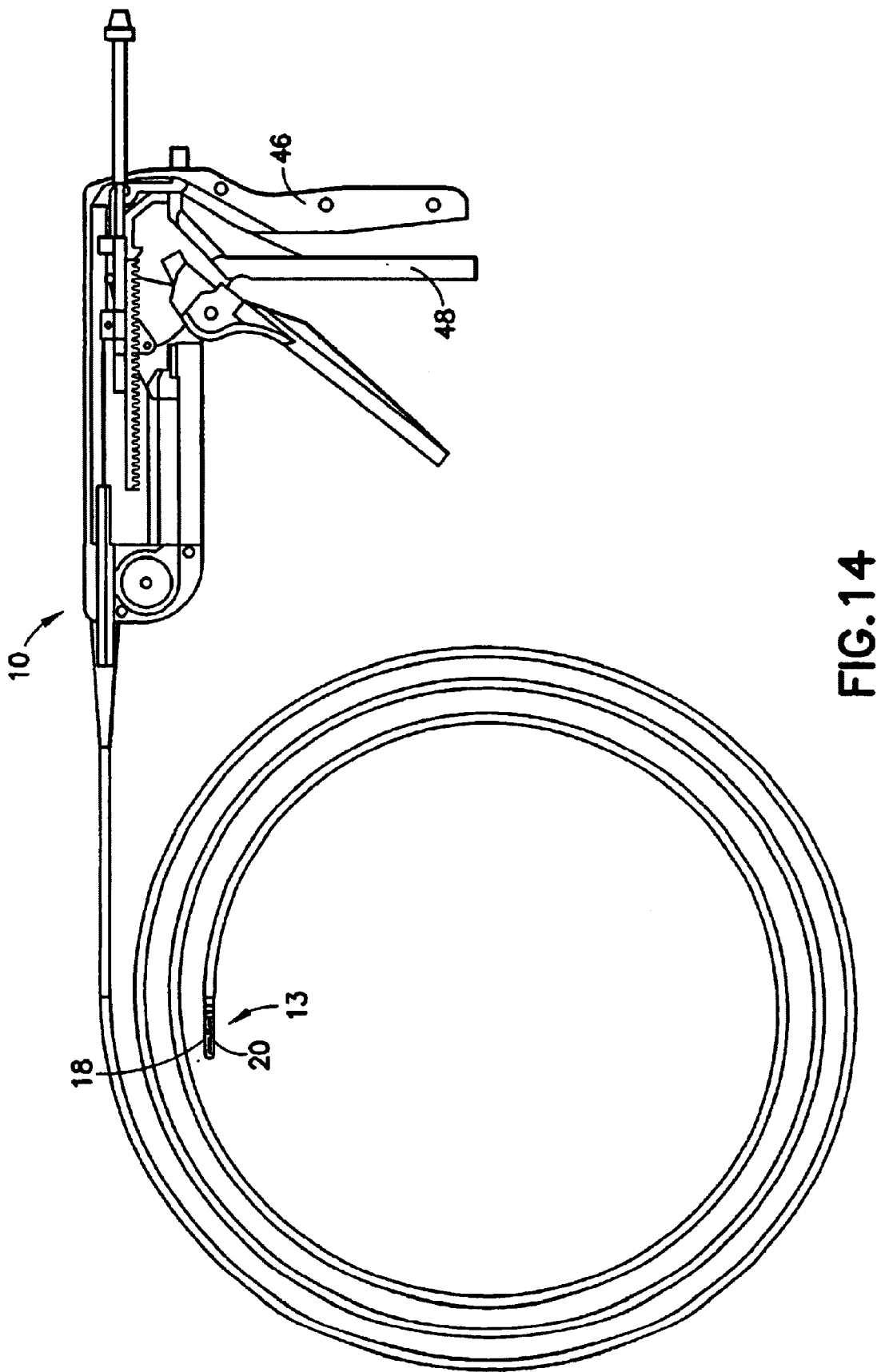
FIG. 14 is a partial section side elevation view of a surgical clip applier according to the invention, showing the jaws in a clamped configuration.

Turning now to FIG. 14, once the jaws 18, 20 of the end effector assembly 13 are positioned on either side of tissue (not shown) about which it is desired to place a clip 202 (FIGS. 2 and 2A), the jaw closing lever 48 is again moved toward the stationary handle 46 to clamp the jaws about the tissue. The lever 48 is moved relatively further than shown in FIG. 12, as the wires 22, 24 will be under load to compress the tissue. Referring back to FIGS. 9 and 10, the teeth 182 on the clamping surfaces 174, 176, 178, 180 of the jaws 18, 20 are angled proximally to pull the tissue into the jaws assembly and securely hold the tissue against the distally directed force of an advanced clip. As the jaws close, the anvil 184 moves between the anvil guides 186, 188, and may partially or fully pierce the tissue.

Once the jaws are fully clamped about the tissue, the locking tooth 90 engages with the lever lock 110 as the latch 94 moves down to allow engagement and thereby lock the jaw closing lever 48 relative to the stationary handle 46, as discussed above with respect to FIGS. 6 and 7. As discussed above, the jaws are locked based upon the load in the handle, rather than at any particular position. This permits locking the jaws about tissues of various thicknesses and compressive properties. Moreover, it is noted that when the jaws 18, 20 are fully clamped, the end effector wires 22, 24 are placed under tension which provides compression to the tubular coil 12 such that the coil has an effectively higher tensile limitation before stretching.

Figure 17:
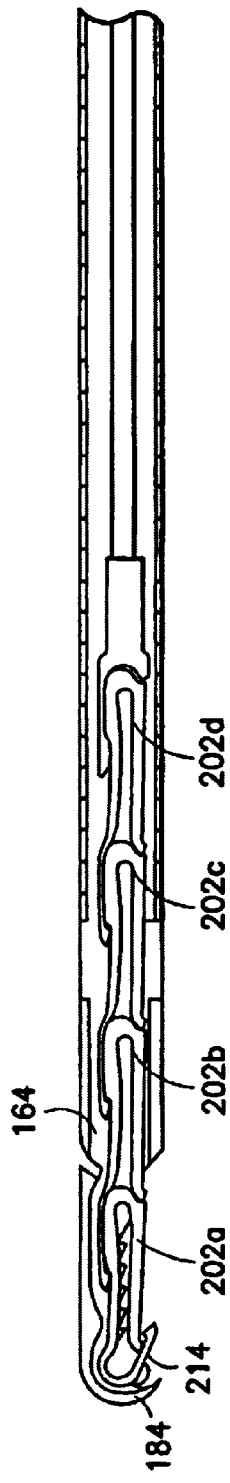
FIG. 17 is a longitudinal section view of the distal end of the clip applier according to the invention, shown with the jaws in a closed configuration and a formed clip therebetween.
Figure 15:
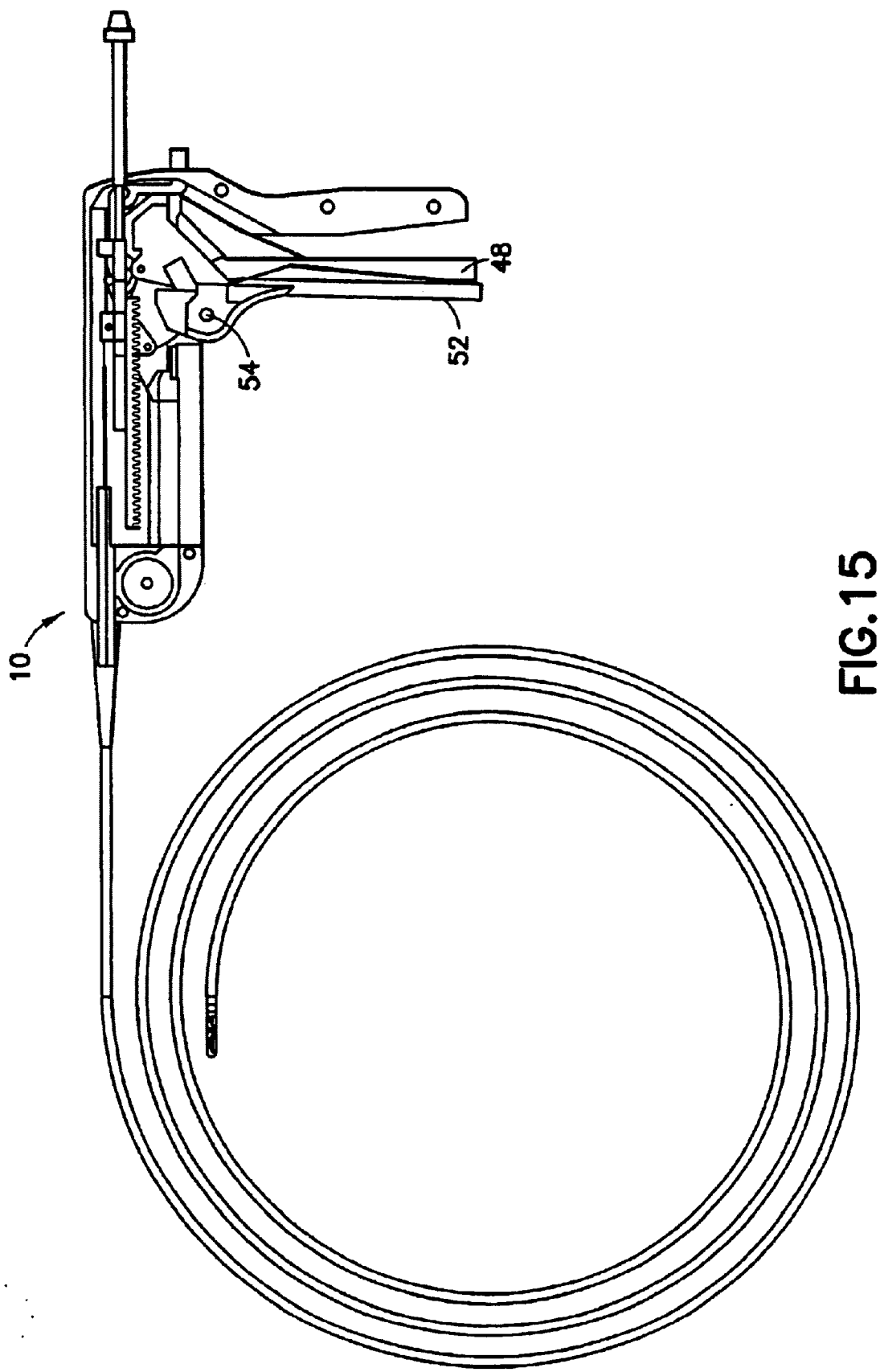
FIG. 15 is a partial section side elevation view of a surgical clip applier according to the invention, showing the jaws in a clamped configuration and the clip-advancing lever actuated.

Referring now to FIGS. 15 and 16, after the jaws are clamped about the tissue, the clip-advancing lever 52 is rotated about the pivot pin 54 to effect advancement of the clip-advancing wire 30 through the tubular coil 12. More particularly, as lever 52 is rotated toward the jaw closing lever 48, the pinion 70 engages the rack 68 to move the rack relatively distally. As the proximal end of the clip-advancing wire 30 is longitudinally fixed relative to the rack 68, the distal end 32 of the clip-advancing wire 30 is consequently moved distally. Referring to FIGS. 10 and 17, the pusher 34, at the distal end 32 of the clip-advancing wire 30 distally advances the clips 202a, 202b, 202c, 202d in the chamber 200, and particularly forces the distalmost clip 202a through the channel 164 in the clevis 14 and between the jaws 18, 20. As clip 202a is further advanced, the first and second arms 204, 206 ride in guides 170, 172, respectively, and are forced over the tissue held between the jaws 18, 20. When the retainer 214 on the first arm 204 of the clip 202a is forced against the anvil 184, the retainer 214 is bent toward jaw 20; the tip 216 pierces the tissue between the jaws 18, 20 (or is guided into the pierce hole made by the anvil 184 when the jaws clamped the tissue); and the tip 216 enters the well 190 at the distal end of jaw 20 to extends around the tip 210 of the second arm 206 which overhangs the well. The hook 218 at the tip 216 of the retainer 214 may engage (although it does not necessarily engage), the latch 212 at the distal end of the second arm 206. The force provided by the clip-advancing wire 30 to advance a clip 202 over the clamped tissue, to bend the retainer 214 against the anvil 184, and to force the tip 216 of the retainer to pierce tissue is at least 500 grams (1.1 lbs), and more typically approaches 1500 grams (3.3 lbs) or higher.

Figure 18:
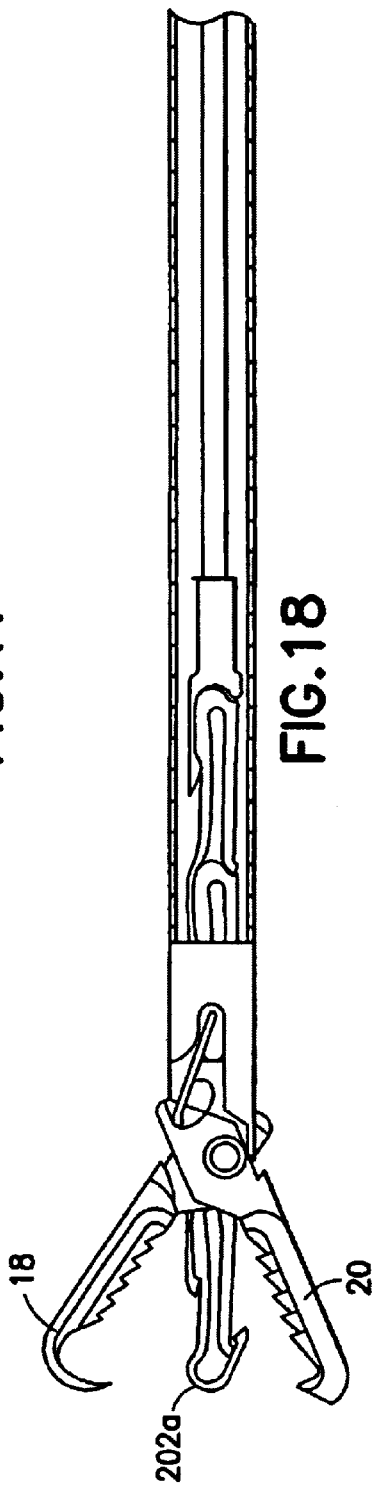
FIG. 18 is a broken partial section side elevation view of the distal end of the clip applier according to the invention, shown with the jaws in an open configuration and a formed clip therebetween.

Referring now to FIGS. 6 and 18, after the clip is applied, the jaws 18, 20 are released from about the tissue. This is done by pressing the release button 124 of the lever lock 110 such that the jaw closing lever 48 is permitted to move relative to the stationary handle 46.

Referring to FIG. 19, the clip is then released from the end effector jaw assembly by moving the jaw assembly relative to the applied clip 202a. The end effector assembly may then be moved to another tissue location to apply additional clips.

Figure 21:
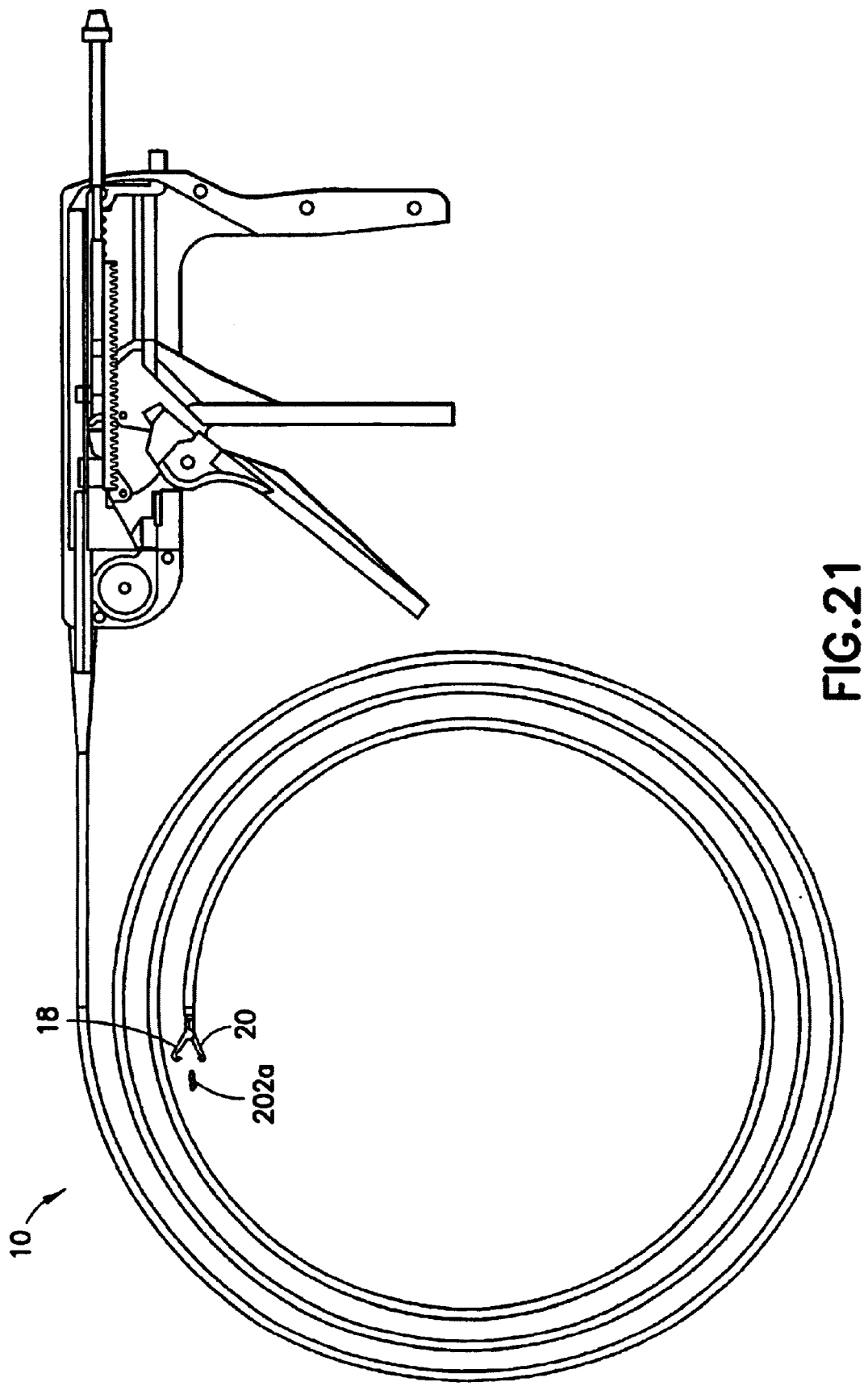
FIG. 21 is a partial section side elevation view of a surgical clip applier according to the invention, shown with the jaws in an open position and a formed clip released therefrom.

It is noted that after clip 202a is released, the retainer 214b of clip 202b partially extends into the space between the jaws 18, 20. If not retracted, this retainer 214b would obstruct positioning the jaws 18, 20 about the tissue and subsequent clip application during the procedure. However, when the clip-advancing lever 52 is released, torsion spring 58 (FIG. 4) operates to pull back the clip-advancing wire 30 and the clip pusher 34 and thereby retract the 'chain' of clips. That is, the clip catch 232 of the clip pusher pulls back on clip 202d, and the retainer 214d of clip 202d pulls back clip 202c, and so on, until the extending retainer 214b is pulled within the chamber 164 of the clevis, and the space between the jaws 18, 20 is cleared, as shown in FIGS. 20 and 21. The clip-advancing wire is limited in the distance by which it can be retracted; it may be retracted only so far as permitted by interference of a ridge 250 on the clip-advancing wire 30 located just distal the catch 256 of the coil connector 152, and the catch 256 (FIG. 2B), which is constructed to be approximately the length of the protruding retainer 214b.

The device may then be used to apply another clip, or the jaws may be closed and the device may be withdrawn through the endoscope.

The resulting clip applier is capable of transmitting a pushing force at the distal end of the clip-advancing wire, resulting from the compressive force appliable to the clip-advancing wire and the relative tensile force appliable to the outer tubular coil and end effector wires, far in excess of the perceived threshold of the 200 grams (0.44 lbs) in the prior art. In fact, as discussed below, one embodiment of the device of the invention provides a pushing force in excess of 2267 grams (5 lbs).

Figure 23:
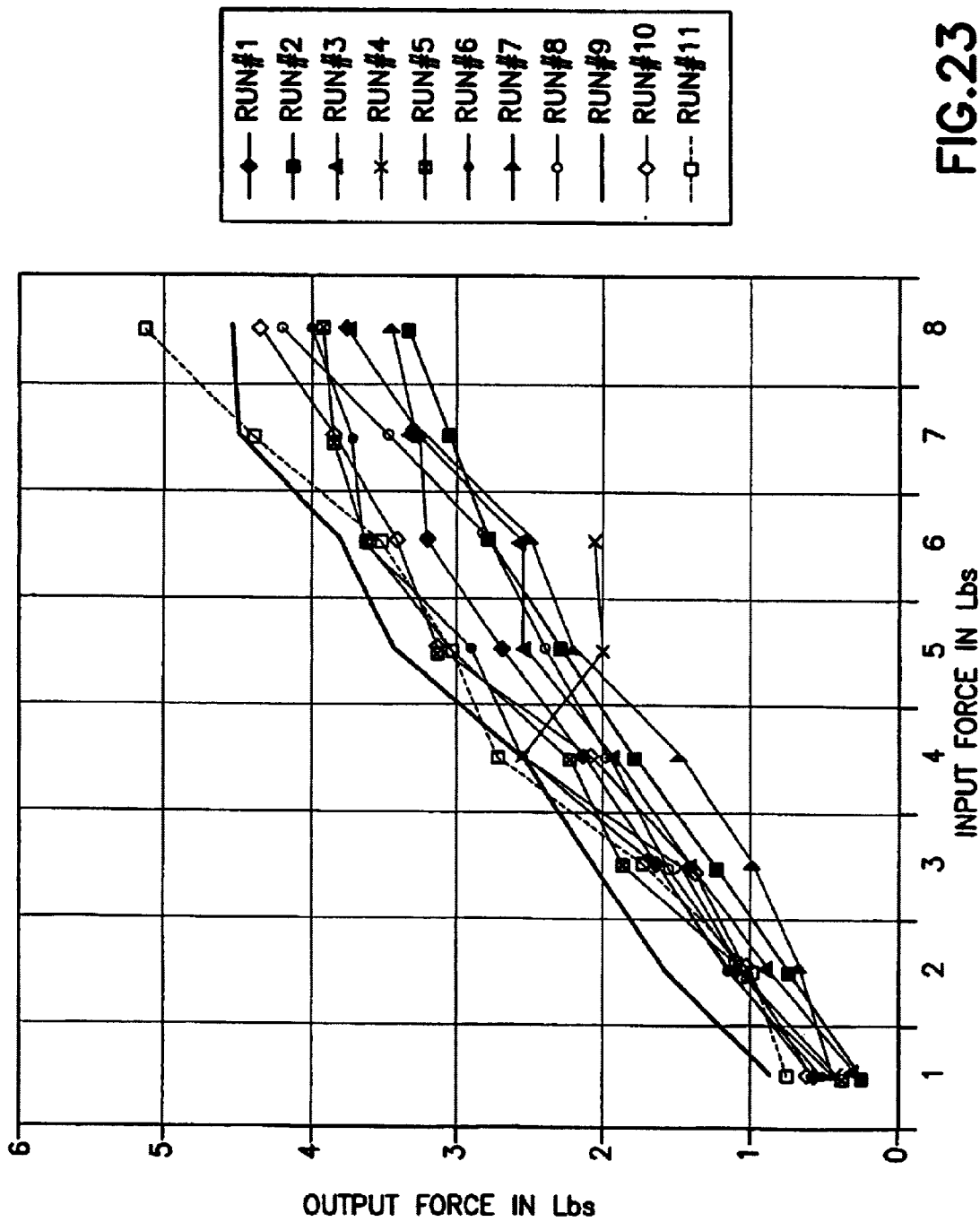
FIG. 23 is an efficiency plot of the prototypes described in the table of FIG. 22.

More particularly, referring to FIG. 22, a table listing part dimensions of six prototype device, and the resultant output forces achieved with prototype devices is provided. FIG. 23 provides an efficiency plot (input pushing force v. output pushing force) for the use of the prototypes. In all prototypes, the tubular coil, clip-advancing wire, and end effector wires are made from stainless steel. Details of the table and the efficiency plot are discussed below with respect to Examples 1 through 6.

EXAMPLE 1

In a first prototype, indicated by 'RUN #1', 'RUN #2' and 'RUN #3', the tubular coil 12 has an outer diameter of 0.09 inch and an inner diameter of 0.06 inch. The clip-advancing wire 30 has an outer diameter of 0.017 inch and the end effector wires 22, 24 each have an outer diameter of 0.011 inch. The proximal end of the end effector wires 22, 24 are pulled with 11 lbs of force which generally results in 5 to 10 lbs of force at the distal end of the end effector wires, depending on the degree to which the tubular coil 12 is bent (modeled by looping the tubular coil through two inch loops); i.e., frictional losses reduce the transmitted force. Moreover, it is noted that whatever force is transmitted to the distal end of the end effector wires 22, 24, only approximately one-fifth of that force is applied to the jaws, as the distance from the jaw tang 168 to the pivot 166 is relatively shorter than the length of the end of the jaw (anvil 184) to the pivot 166, approximately in a one to five ratio. As such, an input force of 11 lbs may results in one to two lbs of force on the jaws 18, 20. Applying the pulling force simulates the in-use condition in which the pushing force is transmitted.

With the tubular coil 12 extending relatively straight (i.e., through no loops) in 'RUN #1', an input pushing force of 8 lbs on the proximal end of the clip-advancing wire 30 (i.e., a pushing force of 8 lbs on the rack 68) resulted in an output pushing force of 3.82 lbs (1732.7 grams) at the clip pusher 34 at the distal end 32 of the clip-advancing wire 30. With the tubular coil 12 extending through one two-inch loop in 'RUN #2', an input pushing force of 8 lbs resulted in an output pushing force of 3.42 lbs (1551.3 grams). With the tubular coil 12 extending through two two-inch loops, in 'RUN #3', an input pushing force of 7 lbs resulted in an output pushing force of 3.37 lbs (1528.6 grams).

EXAMPLE 2

In a second prototype, indicated by 'RUN #4', the diameters of the tubular coil 12 and end effector wires 22, 24 are the same as Example 1. However, the diameter of the clip-advancing wire 30 is decreased to 0.015 inch. With the tubular coil 12 extending through no loops, a six pound input pushing force resulted in an output pushing force of 2.11 lbs (957 grams).

EXAMPLE 3

In a third prototype, indicated by 'RUN #5', 'RUN #6' and 'RUN #7', the diameters of the tubular coil 12 and end effector wires 22, 24 are the same as Example 1. However, the diameter of the clip-advancing wire 30 is increased to 0.02 inch. With the tubular coil 12 extending through no loops in 'RUN #5', an input pushing force of 8 lbs resulted in an output pushing force of 4.03 lbs (1828 grams). With the tubular coil 12 extending through one two-inch loop in 'RUN #6', an input pushing force of 8 lbs resulted in an output pushing force of 4.08 lbs (1851 grams). With the tubular coil extending through two two-inch loops, in 'RUN #7', an input pushing force of 8 lbs resulted in an output pushing force of 3.54 lbs (1605.7 grams).

EXAMPLE 4

In a fourth prototype, indicated by 'RUN #8' and 'RUN #9', the device includes a tubular coil 12 having an outer diameter of 0.086 inch and an inner diameter of 0.053 inch, a clip-advancing wire 30 having a diameter of 0.017 inch, and end effector wires 22, 24 having diameters of 0.009 inch. With the tubular coil extending through no loops, an input pushing force of 8 lbs resulted in 4.61 lbs (2091 grams) of output pushing force. With the tubular coil extending through two two-inch loops, an input pushing force of 8 lbs resulted in 4.28 lbs (1941.3 grams) of output pushing force.

EXAMPLE 5

In a fifth prototype, indicated by 'RUN #10', the clip-advancing wire 30 and end effector wires 22, 24 of the device 10 have the same diameters as Example 4. The tubular coil 12 has an outer diameter of 0.086 inch and an inner diameter of 0.054 inch. With the tubular coil 12 extending through no loops, an input pushing force of 8 lbs resulted in 4.42 lbs (2004.9 grams) of output pushing force.

EXAMPLE 6

In a sixth prototype, indicated by 'RUN #11', the clip-advancing wire 30 and end effector wires 22, 24 of the device 10 have the same diameters as Example 4. The tubular coil 12 has an outer diameter of 0.083 inch and an inner diameter of 0.054 inch. With the tubular coil 12 extending through no loops, an input pushing force of 8 lbs resulted in 5.17 lbs (2345 grams) of output pushing force.

Other flexible clip appliers suitable for use through a relatively smaller 2.6 mm diameter endoscope have also been constructed and tested. For example, one clip applier has a tubular coil 12 with an outer diameter of 0.092 inch, and an inner diameter of 0.060 inch, a clip-advancing wire 30 with a diameter of 0.022 inch, and end effector wires 22, 24 each with a diameter of 0.013 inch. The device can apply a pushing force of between 3 lbs (1361 grams) and 5 lbs (2268 grams) depending on the number of two-inch loops through which the tubular coil was wound.

It is therefore appreciated that other dimensions may be used for devices intended for use in endoscopes having working channels of other sizes. Moreover, the device may be used outside an endoscope, where it is not limited by the size of the working channel.

From the foregoing examples, it will be appreciated that a flexible surgical clip applier, suitable for use through an endoscope is hereby provided. The device is capable of effecting a pushing force far in excess of the previously considered limitation of approximately 200 grams for a mechanical system sized to be used through an endoscope. See C. Paul Swain, "What Endoscopic Accessories Do We Really Need?", Emerging Technologies in Gastrointestinal Endoscopy, *Gastrointest. Endosc.*, Vol. 7, No. 2, pp. 313–330 (April 1997), discussed above. This substantial force permits clips to be forced over tissue and thereby makes available clip clamping, closure, and 'suturing' in an endoscopic procedure.

There have been described and illustrated herein embodiments of a flexible surgical clip applier. While particular embodiments of the invention have been described, it is not intended that the invention be limited thereto, as it is intended that the invention be as broad in scope as the art will allow and that the specification be read likewise. Thus, while particular materials have been disclosed, it will be appreciated that other materials can be used as well. In addition, while particular dimensions have been disclosed, it will be understood that other suitable dimensions can be used as well. Also, while the device has particularly been described for use in endoscopic procedures, where a great need exists for such a device, it will be appreciated that flexible, non-endoscopic devices are considered within the scope of the invention. For example, the tubular coil may have a substantially shorter length and the device may be used through body orifices such as the ear canal, the nasal passages, and through the larynx and trachea. By way of another example, elements of the device may have substantially larger dimensions and the device can be used through a trocar port. Furthermore, while both jaws are shown rotatable about a clevis, it will be appreciated that only one jaw need be rotatable relative to the other. Also, while two clip guides, one on each jaw, are shown, it is recognized that only a single clip guide on one of the jaws is required. Moreover, while the device of the invention is described as having two end effector wires, it will be appreciated that a single control wire may be used which is coupled to at least one of the jaws, and the other jaw may be stationary or mechanically linked to also close and open upon actuation of the single end effector wire. Also, while the device has been described with respect to a clip-advancing wire and end effector wires, it will be appreciated that reference to the 'wires' is intended to also include non-metal filaments, multifilamentary constructs, such as cables, and coils. In addition, while the end effector wires when subject to a tensile force create a compressive force on the tubular coil which effectively increases its tensile capability to facilitate pushing a clip over clamped tissue without exceeding the tensile limitation of the coil, it is recognized that other mechanisms may be used to increase the tensile limitation of the coil. For example, a preferably flat and preferably wire ribbon may be coupled to the inside the coil to limit the amount by which the coil can be stretched. Furthermore, while the ability to provide a relative high pushing force at the distal end of a clip-advancing wire is disclosed with respect to a clip applier, it is recognized that such capability has application to instruments other than clip appliers; for example, for endoscopic staplers, lithotriptors, or any other instrument where it is desired to hold tissue and apply a pushing force, such as a device for tagging. It will therefore be appreciated by those skilled in the art that yet other modifications could be made to the provided invention without deviating from its spirit and scope as claimed.

What is claimed is:

1. A flexible surgical instrument, comprising:
   a) a flexible outer tubular member having proximal and distal ends and defining a longitudinal axis;
   b) a flexible torqueable member extending through said tubular member and having proximal and distal ends;
   c) an attachment means for rotationally securing said flexible torqueable member to a distal end of said tubular member; and
   e) a handle assembly coupled to said proximal ends of said tubular member and said flexible torqueable member and adapted to torque said proximal end of said flexible torqueable member relative to said tubular member which, through said attachment means, causes said distal end of said outer tubular member to rotate.

2. A flexible surgical instrument according to claim 1, wherein:
   said tubular member is a tubular coil.

3. A flexible surgical instrument according to claim 1, wherein:
   said tubular coil is a flat wire wound coil.

4. A flexible surgical instrument according to claim 1, wherein:
   said attachment means includes a connector fixedly coupled with said distal end of said tubular member, said connector defining a keyhole, and a key element provided at said distal end of said flexible member, said key element extending through said keyhole and defining a rotationally interfering key for said keyhole.

5. A flexible surgical instrument according to claim 4, wherein:
   said key element of said flexible torqueable member is longitudinally movable relative to said keyhole of said connector.

6. A flexible surgical instrument according to claim 4, wherein:
   said connector includes a catch, and said flexible torqueable member includes a plurality of structures which interfere with said catch when any one of said structures is attempted to be moved proximally relative to said catch to thereby substantially prevent proximal movement of said flexible torqueable member a distance which would cause one of the structures located distal of the catch to be moved proximal of said catch.

7. A flexible surgical instrument according to claim 6, wherein:
   said catch permits movement of said structures distally past said catch.

8. A flexible surgical instrument according to claim 1, wherein:
   said tubular member is a coil including a plurality of turns, and said coil is preloaded such that each turn in said coil is substantially in contact with an adjacent turn 360° around said coil.

9. A flexible surgical instrument according to claim 1, further comprising:
   f) an inner sheath extending within said tubular member between said handle and said connector, said sheath having a non-circular cross-section and including a lumen through which said flexible torqueable member extends.

10. A flexible surgical instrument according to claim 1, wherein:
    said flexible torqueable member is longitudinally movable relative to said attachment means.

11. A flexible surgical instrument according to claim 1, wherein:
    said handle assembly includes a stationary handle and a rotation knob extending relative to said stationary handle, said rotation knob also being coupled to said proximal end of said flexible torqueable member, wherein rotation of said knob causes a torque to be applied to said proximal end of said flexible torqueable member.

12. A flexible surgical instrument according to claim 11, wherein:
    said rotation knob is telescopically coupled to said proximal end of said flexible torqueable member, such that when said flexible torqueable member is moved longitudinally through said tubular member, said rotation knob remains at a fixed extension relative to said stationary handle.

13. A flexible surgical instrument according to claim 1, further comprising:
    f) an end effector assembly coupled to said distal end of said tubular member; and
    g) at least one end effector control element extending through said tubular member and having proximal and distal ends, said distal end coupled to said end effector assembly and said proximal end coupled to said handle assembly, said handle assembly being adapted to move said at least one end effector control element relative to said tubular member to effect operation of said end effector assembly.

14. A flexible surgical instrument according to claim 13, wherein:
    said end effector assembly includes a jaw mount defining a channel, and a pair of jaws, at least one of said jaws of said pair of jaws being rotatable on said jaw mount relative to the other of said jaws.

15. A flexible surgical instrument according to claim 14, further comprising:
    h) a clip chamber formed by at least one of said tubular member and said end effector assembly, said clip chamber adapted to store at least one surgical clip,
    wherein when said handle is operated to cause said flexible torqueable member to be forced distally relative to said tubular member, sufficient force is provided by said flexible torqueable member to move a surgical clip over the clamped tissue.

16. A flexible surgical instrument according to claim 15, wherein:
    said clip chamber is at least partially formed by said tubular member, and is adapted to store a plurality of clips.

* * * * *